(12) United States Patent
Kane et al.

(10) Patent No.: US 10,226,631 B2
(45) Date of Patent: Mar. 12, 2019

(54) SYSTEMS AND METHODS FOR INFARCT DETECTION

(71) Applicant: Cardiac Pacemakers, Inc., St. Paul, MN (US)

(72) Inventors: Michael J. Kane, Roseville, MN (US); Allan Charles Shuros, St. Paul, MN (US); Brian L. Schmidt, White Bear Lake, MN (US); Keith R. Maile, New Brighton, MN (US); Benjamin J. Haasl, Forest Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 196 days.

(21) Appl. No.: 15/244,740

(22) Filed: Aug. 23, 2016

(65) Prior Publication Data

US 2017/0056667 A1 Mar. 2, 2017

Related U.S. Application Data

(60) Provisional application No. 62/211,397, filed on Aug. 28, 2015.

(51) Int. Cl.
*A61N 1/365* (2006.01)
*A61B 5/11* (2006.01)
(Continued)

(52) U.S. Cl.
CPC ........ *A61N 1/36578* (2013.01); *A61B 5/0004* (2013.01); *A61B 5/0022* (2013.01);
(Continued)

(58) Field of Classification Search
CPC .............. A61N 1/36578; A61B 5/0004; A61B 5/0022; A61B 5/0031; A61B 5/0255;
(Continued)

(56) References Cited

U.S. PATENT DOCUMENTS 3,835,864 A 9/1974 Rasor et al.
3,943,936 A 3/1976 Rasor et al.
(Continued)

FOREIGN PATENT DOCUMENTS

AU 2008279789 B2 10/2011
AU 2008329620 B2 5/2014
(Continued)

OTHER PUBLICATIONS

US 8,886,318, 11/2014, Jacobson et al. (withdrawn)
(Continued)

*Primary Examiner* — Paula J Stice
(74) *Attorney, Agent, or Firm* — Seager, Tufte & Wickhem LLP

(57) ABSTRACT

Systems, devices, and methods for determining occurrences of myocardial infarctions are disclosed. In one embodiment, a method of sensing for an occurrence of a myocardial infarction may include sensing a baseline accelerometer signal during a baseline, determining a baseline template based on one or more characteristics of the baseline accelerometer signal, and storing the baseline template in a memory. The method may further include sensing an accelerometer signal during a test period subsequent to the baseline, determining a test template based on one or more characteristics of the accelerometer signal during the test period, and comparing the baseline template with the test template, and based on the comparison, determining if a myocardial infarction occurred in the patient's heart. If it is determined that a myocardial infarction occurred in the patient's heart, the method may further include displaying an indication on a display that a myocardial infarction occurred.

16 Claims, 12 Drawing Sheets

(51) Int. Cl.
*A61B 5/00* (2006.01)
*A61B 5/0255* (2006.01)

(52) U.S. Cl.
CPC .......... *A61B 5/0031* (2013.01); *A61B 5/0255* (2013.01); *A61B 5/1102* (2013.01); *A61B 5/1118* (2013.01); *A61B 5/686* (2013.01); *A61B 5/7246* (2013.01); *A61B 5/742* (2013.01); *A61B 2562/0219* (2013.01)

(58) Field of Classification Search
CPC ..... A61B 5/1102; A61B 5/1118; A61B 5/686; A61B 5/7246; A61B 5/742
See application file for complete search history.

(56) References Cited

U.S. PATENT DOCUMENTS

| | | |
|---|---|---|
| 4,142,530 A | 3/1979 | Wittkampf |
| 4,151,513 A | 4/1979 | Menken et al. |
| 4,157,720 A | 6/1979 | Greatbatch |
| RE30,366 E | 8/1980 | Rasor et al. |
| 4,243,045 A | 1/1981 | Maas |
| 4,250,884 A | 2/1981 | Hartlaub et al. |
| 4,256,115 A | 3/1981 | Bilitch |
| 4,263,919 A | 4/1981 | Levin |
| 4,310,000 A | 1/1982 | Lindemans |
| 4,312,354 A | 1/1982 | Walters |
| 4,323,081 A | 4/1982 | Wiebusch |
| 4,357,946 A | 11/1982 | Dutcher et al. |
| 4,365,639 A | 12/1982 | Goldreyer |
| 4,440,173 A | 4/1984 | Hudziak et al. |
| 4,476,868 A | 10/1984 | Thompson |
| 4,522,208 A | 6/1985 | Buffet |
| 4,537,200 A | 8/1985 | Widrow |
| 4,556,063 A | 12/1985 | Thompson et al. |
| 4,562,841 A | 1/1986 | Brockway et al. |
| 4,593,702 A | 6/1986 | Kepski et al. |
| 4,593,955 A | 6/1986 | Leiber |
| 4,630,611 A | 12/1986 | King |
| 4,635,639 A | 1/1987 | Hakala et al. |
| 4,674,508 A | 6/1987 | DeCote |
| 4,712,554 A | 12/1987 | Garson |
| 4,729,376 A | 3/1988 | DeCote |
| 4,754,753 A | 7/1988 | King |
| 4,759,366 A | 7/1988 | Callaghan |
| 4,776,338 A | 10/1988 | Lekholm et al. |
| 4,787,389 A | 11/1988 | Tarjan |
| 4,793,353 A | 12/1988 | Borkan |
| 4,819,662 A | 4/1989 | Heil et al. |
| 4,858,610 A | 8/1989 | Callaghan et al. |
| 4,886,064 A | 12/1989 | Strandberg |
| 4,887,609 A | 12/1989 | Cole, Jr. |
| 4,928,688 A | 5/1990 | Mower |
| 4,967,746 A | 11/1990 | Vandegriff |
| 4,987,897 A | 1/1991 | Funke |
| 4,989,602 A | 2/1991 | Sholder et al. |
| 5,012,806 A | 5/1991 | De Bellis |
| 5,036,849 A | 8/1991 | Hauck et al. |
| 5,040,534 A | 8/1991 | Mann et al. |
| 5,058,581 A | 10/1991 | Silvian |
| 5,078,134 A | 1/1992 | Heilman et al. |
| 5,109,845 A | 5/1992 | Yuuchi et al. |
| 5,113,859 A | 5/1992 | Funke |
| 5,117,824 A | 6/1992 | Keimel et al. |
| 5,127,401 A | 7/1992 | Grevious et al. |
| 5,133,353 A | 7/1992 | Hauser |
| 5,144,950 A | 9/1992 | Stoop et al. |
| 5,170,784 A | 12/1992 | Ramon et al. |
| 5,179,945 A | 1/1993 | Van Hofwegen et al. |
| 5,193,539 A | 3/1993 | Schulman et al. |
| 5,193,540 A | 3/1993 | Schulman et al. |
| 5,241,961 A | 9/1993 | Henry |
| 5,243,977 A | 9/1993 | Trabucco et al. |
| 5,259,387 A | 11/1993 | dePinto |
| 5,269,326 A | 12/1993 | Verrier |
| 5,284,136 A | 2/1994 | Hauck et al. |
| 5,300,107 A | 4/1994 | Stokes et al. |
| 5,301,677 A | 4/1994 | Hsung |
| 5,305,760 A | 4/1994 | McKown et al. |
| 5,312,439 A | 5/1994 | Loeb |
| 5,313,953 A | 5/1994 | Yomtov et al. |
| 5,314,459 A | 5/1994 | Swanson et al. |
| 5,318,597 A | 6/1994 | Hauck et al. |
| 5,324,316 A | 6/1994 | Schulman et al. |
| 5,331,966 A | 7/1994 | Bennett et al. |
| 5,334,222 A | 8/1994 | Salo et al. |
| 5,342,408 A | 8/1994 | Decoriolis et al. |
| 5,370,667 A | 12/1994 | Alt |
| 5,372,606 A | 12/1994 | Lang et al. |
| 5,376,106 A | 12/1994 | Stahmann et al. |
| 5,383,915 A | 1/1995 | Adams |
| 5,388,578 A | 2/1995 | Yomtov et al. |
| 5,404,877 A | 4/1995 | Nolan et al. |
| 5,405,367 A | 4/1995 | Schulman et al. |
| 5,411,031 A | 5/1995 | Yomtov |
| 5,411,525 A | 5/1995 | Swanson et al. |
| 5,411,535 A | 5/1995 | Fujii et al. |
| 5,456,691 A | 10/1995 | Snell |
| 5,458,622 A | 10/1995 | Alt |
| 5,466,246 A | 11/1995 | Silvian |
| 5,468,254 A | 11/1995 | Hahn et al. |
| 5,472,453 A | 12/1995 | Alt |
| 5,522,866 A | 6/1996 | Fernald |
| 5,540,727 A | 7/1996 | Tockman et al. |
| 5,545,186 A | 8/1996 | Olson et al. |
| 5,545,202 A | 8/1996 | Dahl et al. |
| 5,571,146 A | 11/1996 | Jones et al. |
| 5,591,214 A | 1/1997 | Lu |
| 5,620,466 A | 4/1997 | Haefner et al. |
| 5,634,938 A | 6/1997 | Swanson et al. |
| 5,649,968 A | 7/1997 | Alt et al. |
| 5,662,688 A | 9/1997 | Haefner et al. |
| 5,674,259 A | 10/1997 | Gray |
| 5,683,426 A | 11/1997 | Greenhut et al. |
| 5,683,432 A | 11/1997 | Goedeke et al. |
| 5,706,823 A | 1/1998 | Wodlinger |
| 5,709,215 A | 1/1998 | Perttu et al. |
| 5,720,770 A | 2/1998 | Nappholz et al. |
| 5,728,154 A | 3/1998 | Crossett et al. |
| 5,741,314 A | 4/1998 | Daly et al. |
| 5,741,315 A | 4/1998 | Lee et al. |
| 5,752,976 A | 5/1998 | Duffin et al. |
| 5,752,977 A | 5/1998 | Grevious et al. |
| 5,755,736 A | 5/1998 | Gillberg et al. |
| 5,759,199 A | 6/1998 | Snell et al. |
| 5,774,501 A | 6/1998 | Halpern et al. |
| 5,792,195 A | 8/1998 | Carlson et al. |
| 5,792,202 A | 8/1998 | Rueter |
| 5,792,203 A | 8/1998 | Schroeppel |
| 5,792,205 A | 8/1998 | Alt et al. |
| 5,792,208 A | 8/1998 | Gray |
| 5,814,089 A | 9/1998 | Stokes et al. |
| 5,827,216 A | 10/1998 | Igo et al. |
| 5,836,985 A | 11/1998 | Goyal et al. |
| 5,836,987 A | 11/1998 | Baumann et al. |
| 5,842,977 A | 12/1998 | Lesho et al. |
| 5,855,593 A | 1/1999 | Olson et al. |
| 5,873,894 A | 2/1999 | Vandegriff et al. |
| 5,891,184 A | 4/1999 | Lee et al. |
| 5,897,586 A | 4/1999 | Molina |
| 5,899,876 A | 5/1999 | Flower |
| 5,899,928 A | 5/1999 | Sholder et al. |
| 5,919,214 A | 7/1999 | Ciciarelli et al. |
| 5,935,078 A | 8/1999 | Feierbach |
| 5,941,906 A | 8/1999 | Barreras et al. |
| 5,944,744 A | 8/1999 | Paul et al. |
| 5,954,757 A | 9/1999 | Gray |
| 5,978,713 A | 11/1999 | Prutchi et al. |
| 5,991,660 A | 11/1999 | Goyal |
| 5,991,661 A | 11/1999 | Park et al. |
| 5,999,848 A | 12/1999 | Gord et al. |
| 5,999,857 A | 12/1999 | Weijand et al. |
| 6,016,445 A | 1/2000 | Baura |
| 6,026,320 A | 2/2000 | Carlson et al. |

(56) References Cited

U.S. PATENT DOCUMENTS

| | | |
|---|---|---|
| 6,029,085 A | 2/2000 | Olson et al. |
| 6,041,250 A | 3/2000 | dePinto |
| 6,044,298 A | 3/2000 | Salo et al. |
| 6,044,299 A | 3/2000 | Nilsson |
| 6,044,300 A | 3/2000 | Gray |
| 6,055,454 A | 4/2000 | Heemels |
| 6,073,050 A | 6/2000 | Griffith |
| 6,076,016 A | 6/2000 | Feierbach |
| 6,077,236 A | 6/2000 | Cunningham |
| 6,080,187 A | 6/2000 | Alt et al. |
| 6,083,248 A | 7/2000 | Thompson |
| 6,106,551 A | 8/2000 | Crossett et al. |
| 6,115,636 A | 9/2000 | Ryan |
| 6,128,526 A | 10/2000 | Stadler et al. |
| 6,141,581 A | 10/2000 | Olson et al. |
| 6,141,588 A | 10/2000 | Cox et al. |
| 6,141,592 A | 10/2000 | Pauly |
| 6,144,879 A | 11/2000 | Gray |
| 6,162,195 A | 12/2000 | Igo et al. |
| 6,164,284 A | 12/2000 | Schulman et al. |
| 6,167,310 A | 12/2000 | Grevious |
| 6,201,993 B1 | 3/2001 | Kruse et al. |
| 6,208,894 B1 | 3/2001 | Schulman et al. |
| 6,211,799 B1 | 4/2001 | Post et al. |
| 6,217,525 B1 | 4/2001 | Medema et al. |
| 6,221,011 B1 | 4/2001 | Bardy |
| 6,240,316 B1 | 5/2001 | Richmond et al. |
| 6,240,317 B1 | 5/2001 | Villaseca et al. |
| 6,256,534 B1 | 7/2001 | Dahl |
| 6,259,947 B1 | 7/2001 | Olson et al. |
| 6,266,558 B1 | 7/2001 | Gozani et al. |
| 6,266,567 B1 | 7/2001 | Ishikawa et al. |
| 6,270,457 B1 | 8/2001 | Bardy |
| 6,272,377 B1 | 8/2001 | Sweeney et al. |
| 6,273,856 B1 | 8/2001 | Sun et al. |
| 6,277,072 B1 | 8/2001 | Bardy |
| 6,280,380 B1 | 8/2001 | Bardy |
| 6,285,907 B1 | 9/2001 | Kramer et al. |
| 6,292,698 B1 | 9/2001 | Duffin et al. |
| 6,295,473 B1 | 9/2001 | Rosar |
| 6,297,943 B1 | 10/2001 | Carson |
| 6,298,271 B1 | 10/2001 | Weijand |
| 6,307,751 B1 | 10/2001 | Bodony et al. |
| 6,312,378 B1 | 11/2001 | Bardy |
| 6,315,721 B2 | 11/2001 | Schulman et al. |
| 6,336,903 B1 | 1/2002 | Bardy |
| 6,345,202 B2 | 2/2002 | Richmond et al. |
| 6,351,667 B1 | 2/2002 | Godie |
| 6,351,669 B1 | 2/2002 | Hartley et al. |
| 6,353,759 B1 | 3/2002 | Hartley et al. |
| 6,358,203 B2 | 3/2002 | Bardy |
| 6,361,780 B1 | 3/2002 | Ley et al. |
| 6,368,284 B1 | 4/2002 | Bardy |
| 6,371,922 B1 | 4/2002 | Baumann et al. |
| 6,398,728 B1 | 6/2002 | Bardy |
| 6,400,982 B2 | 6/2002 | Sweeney et al. |
| 6,400,990 B1 | 6/2002 | Silvian |
| 6,408,208 B1 | 6/2002 | Sun |
| 6,409,674 B1 | 6/2002 | Brockway et al. |
| 6,411,848 B2 | 6/2002 | Kramer et al. |
| 6,424,865 B1 | 7/2002 | Ding |
| 6,434,429 B1 | 8/2002 | Kraus et al. |
| 6,438,410 B2 | 8/2002 | Hsu et al. |
| 6,438,417 B1 | 8/2002 | Rockwell et al. |
| 6,438,421 B1 | 8/2002 | Stahmann et al. |
| 6,440,066 B1 | 8/2002 | Bardy |
| 6,441,747 B1 | 8/2002 | Khair et al. |
| 6,442,426 B1 | 8/2002 | Kroll |
| 6,442,432 B2 | 8/2002 | Lee |
| 6,443,891 B1 | 9/2002 | Grevious |
| 6,445,953 B1 | 9/2002 | Bulkes et al. |
| 6,449,508 B1 | 9/2002 | Sheldon et al. |
| 6,453,200 B1 | 9/2002 | Koslar |
| 6,459,929 B1 | 10/2002 | Hopper et al. |
| 6,470,215 B1 | 10/2002 | Kraus et al. |
| 6,471,645 B1 | 10/2002 | Warkentin et al. |
| 6,480,745 B2 | 11/2002 | Nelson et al. |
| 6,487,443 B2 | 11/2002 | Olson et al. |
| 6,490,487 B1 | 12/2002 | Kraus et al. |
| 6,498,951 B1 | 12/2002 | Larson et al. |
| 6,507,755 B1 | 1/2003 | Gozani et al. |
| 6,507,759 B1 | 1/2003 | Prutchi et al. |
| 6,512,940 B1 | 1/2003 | Brabec et al. |
| 6,522,915 B1 | 2/2003 | Ceballos et al. |
| 6,526,311 B2 | 2/2003 | Begemann |
| 6,539,253 B2 | 3/2003 | Thompson et al. |
| 6,542,775 B2 | 4/2003 | Ding et al. |
| 6,553,258 B2 | 4/2003 | Stahmann et al. |
| 6,561,975 B1 | 5/2003 | Pool et al. |
| 6,564,807 B1 | 5/2003 | Schulman et al. |
| 6,574,506 B2 | 6/2003 | Kramer et al. |
| 6,584,351 B1 | 6/2003 | Ekwall |
| 6,584,352 B2 | 6/2003 | Combs et al. |
| 6,597,948 B1 | 7/2003 | Rockwell et al. |
| 6,597,951 B2 | 7/2003 | Kramer et al. |
| 6,622,046 B2 | 9/2003 | Fraley et al. |
| 6,628,985 B2 | 9/2003 | Sweeney et al. |
| 6,647,292 B1 | 11/2003 | Bardy et al. |
| 6,658,292 B2 | 12/2003 | Kroll et al. |
| 6,666,844 B1 | 12/2003 | Igo et al. |
| 6,689,117 B2 | 2/2004 | Sweeney et al. |
| 6,690,959 B2 | 2/2004 | Thompson |
| 6,694,189 B2 | 2/2004 | Begemann |
| 6,704,602 B2 | 3/2004 | Berg et al. |
| 6,718,212 B2 | 4/2004 | Parry et al. |
| 6,721,597 B1 | 4/2004 | Bardy et al. |
| 6,738,670 B1 | 5/2004 | Almendinger et al. |
| 6,746,797 B2 | 6/2004 | Benson et al. |
| 6,749,566 B2 | 6/2004 | Russ |
| 6,758,810 B2 | 7/2004 | Lebel et al. |
| 6,763,269 B2 | 7/2004 | Cox |
| 6,778,860 B2 | 8/2004 | Ostroff et al. |
| 6,788,971 B1 | 9/2004 | Sloman et al. |
| 6,788,974 B2 | 9/2004 | Bardy et al. |
| 6,804,558 B2 | 10/2004 | Haller et al. |
| 6,807,442 B1 | 10/2004 | Myklebust et al. |
| 6,847,844 B2 | 1/2005 | Sun et al. |
| 6,871,095 B2 | 3/2005 | Stahmann et al. |
| 6,878,112 B2 | 4/2005 | Linberg et al. |
| 6,885,889 B2 | 4/2005 | Chinchoy |
| 6,892,094 B2 | 5/2005 | Ousdigian et al. |
| 6,897,788 B2 | 5/2005 | Khair et al. |
| 6,904,315 B2 | 6/2005 | Panken et al. |
| 6,922,592 B2 | 7/2005 | Thompson et al. |
| 6,931,282 B2 | 8/2005 | Esler |
| 6,934,585 B1 | 8/2005 | Schloss et al. |
| 6,937,899 B2 | 8/2005 | Sheldon et al. |
| 6,957,107 B2 | 10/2005 | Rogers et al. |
| 6,978,176 B2 | 12/2005 | Lattouf |
| 6,985,773 B2 | 1/2006 | Von Arx et al. |
| 6,990,375 B2 | 1/2006 | Kloss et al. |
| 7,001,366 B2 | 2/2006 | Ballard |
| 7,003,350 B2 | 2/2006 | Denker et al. |
| 7,006,864 B2 | 2/2006 | Echt et al. |
| 7,013,178 B2 | 3/2006 | Reinke et al. |
| 7,027,871 B2 | 4/2006 | Burnes et al. |
| 7,050,849 B2 | 5/2006 | Echt et al. |
| 7,060,031 B2 | 6/2006 | Webb et al. |
| 7,063,693 B2 | 6/2006 | Guenst |
| 7,082,336 B2 | 7/2006 | Ransbury et al. |
| 7,085,606 B2 | 8/2006 | Flach et al. |
| 7,092,758 B2 | 8/2006 | Sun et al. |
| 7,110,824 B2 | 9/2006 | Amundson et al. |
| 7,120,504 B2 | 10/2006 | Osypka |
| 7,130,681 B2 | 10/2006 | Gebhardt et al. |
| 7,139,613 B2 | 11/2006 | Reinke et al. |
| 7,142,912 B2 | 11/2006 | Wagner et al. |
| 7,146,225 B2 | 12/2006 | Guenst et al. |
| 7,146,226 B2 | 12/2006 | Lau et al. |
| 7,149,581 B2 | 12/2006 | Goedeke |
| 7,149,588 B2 | 12/2006 | Lau et al. |
| 7,158,839 B2 | 1/2007 | Lau |
| 7,162,307 B2 | 1/2007 | Patrias |
| 7,164,952 B2 | 1/2007 | Lau et al. |

(56) References Cited

U.S. PATENT DOCUMENTS

| | | | |
|---|---|---|---|
| 7,177,700 B1 | 2/2007 | Cox |
| 7,181,268 B2 | 2/2007 | Sheldon et al. |
| 7,181,505 B2 | 2/2007 | Haller et al. |
| 7,184,830 B2 | 2/2007 | Echt et al. |
| 7,186,214 B2 | 3/2007 | Ness |
| 7,191,015 B2 | 3/2007 | Lamson et al. |
| 7,200,437 B1 | 4/2007 | Nabutovsky et al. |
| 7,200,439 B2 | 4/2007 | Zdeblick et al. |
| 7,206,423 B1 | 4/2007 | Feng et al. |
| 7,209,785 B2 | 4/2007 | Kim et al. |
| 7,209,790 B2 | 4/2007 | Thompson et al. |
| 7,211,884 B1 | 5/2007 | Davis et al. |
| 7,212,871 B1 | 5/2007 | Morgan |
| 7,226,440 B2 | 6/2007 | Gelfand et al. |
| 7,228,183 B2 | 6/2007 | Sun et al. |
| 7,236,821 B2 | 6/2007 | Cates et al. |
| 7,236,829 B1 | 6/2007 | Farazi et al. |
| 7,254,448 B2 | 8/2007 | Almendinger et al. |
| 7,260,436 B2 | 8/2007 | Kilgore et al. |
| 7,270,669 B1 | 9/2007 | Sra |
| 7,272,448 B1 | 9/2007 | Morgan et al. |
| 7,277,755 B1 | 10/2007 | Falkenberg et al. |
| 7,280,872 B1 | 10/2007 | Mosesov et al. |
| 7,288,096 B2 | 10/2007 | Chin |
| 7,289,847 B1 | 10/2007 | Gill et al. |
| 7,289,852 B2 | 10/2007 | Helfinstine et al. |
| 7,289,853 B1 | 10/2007 | Campbell et al. |
| 7,289,855 B2 | 10/2007 | Nghiem et al. |
| 7,302,294 B2 | 11/2007 | Kamath et al. |
| 7,305,266 B1 | 12/2007 | Kroll |
| 7,310,556 B2 | 12/2007 | Bulkes |
| 7,319,905 B1 | 1/2008 | Morgan et al. |
| 7,333,853 B2 | 2/2008 | Mazar et al. |
| 7,336,994 B2 | 2/2008 | Hettrick et al. |
| 7,347,819 B2 | 3/2008 | Lebel et al. |
| 7,366,572 B2 | 4/2008 | Heruth et al. |
| 7,373,207 B2 | 5/2008 | Lattouf |
| 7,384,403 B2 | 6/2008 | Sherman |
| 7,386,342 B1 | 6/2008 | Falkenberg et al. |
| 7,392,090 B2 | 6/2008 | Sweeney et al. |
| 7,406,105 B2 | 7/2008 | DelMain et al. |
| 7,406,349 B2 | 7/2008 | Seeberger et al. |
| 7,410,497 B2 | 8/2008 | Hastings et al. |
| 7,425,200 B2 | 9/2008 | Brockway et al. |
| 7,433,739 B1 | 10/2008 | Salys et al. |
| 7,496,409 B2 | 2/2009 | Greenhut et al. |
| 7,496,410 B2 | 2/2009 | Heil |
| 7,502,652 B2 | 3/2009 | Gaunt et al. |
| 7,512,448 B2 | 3/2009 | Malick et al. |
| 7,515,969 B2 | 4/2009 | Tockman et al. |
| 7,526,342 B2 | 4/2009 | Chin et al. |
| 7,529,589 B2 | 5/2009 | Williams et al. |
| 7,532,933 B2 | 5/2009 | Hastings et al. |
| 7,536,222 B2 | 5/2009 | Bardy et al. |
| 7,536,224 B2 | 5/2009 | Ritscher et al. |
| 7,539,541 B2 | 5/2009 | Quiles et al. |
| 7,544,197 B2 | 6/2009 | Kelsch et al. |
| 7,558,631 B2 | 7/2009 | Cowan et al. |
| 7,565,195 B1 | 7/2009 | Kroll et al. |
| 7,569,020 B2 | 8/2009 | Norén et al. |
| 7,584,002 B2 | 9/2009 | Burnes et al. |
| 7,590,455 B2 | 9/2009 | Heruth et al. |
| 7,606,621 B2 | 10/2009 | Brisken et al. |
| 7,610,088 B2 | 10/2009 | Chinchoy |
| 7,610,092 B2 | 10/2009 | Cowan et al. |
| 7,610,099 B2 | 10/2009 | Almendinger et al. |
| 7,610,104 B2 | 10/2009 | Kaplan et al. |
| 7,616,991 B2 | 11/2009 | Mann et al. |
| 7,617,001 B2 | 11/2009 | Penner et al. |
| 7,617,007 B2 | 11/2009 | Williams et al. |
| 7,630,767 B1 | 12/2009 | Poore et al. |
| 7,634,313 B1 | 12/2009 | Kroll et al. |
| 7,637,867 B2 | 12/2009 | Zdeblick |
| 7,640,060 B2 | 12/2009 | Zdeblick |
| 7,647,109 B2 | 1/2010 | Hastings et al. |
| 7,650,186 B2 | 1/2010 | Hastings et al. |
| 7,657,311 B2 | 2/2010 | Bardy et al. |
| 7,662,086 B2 | 2/2010 | Björling |
| 7,668,596 B2 | 2/2010 | Von Arx et al. |
| 7,682,316 B2 | 3/2010 | Anderson et al. |
| 7,691,047 B2 | 4/2010 | Ferrari |
| 7,702,392 B2 | 4/2010 | Echt et al. |
| 7,713,194 B2 | 5/2010 | Zdeblick |
| 7,713,195 B2 | 5/2010 | Zdeblick |
| 7,729,783 B2 | 6/2010 | Michels et al. |
| 7,734,333 B2 | 6/2010 | Ghanem et al. |
| 7,734,343 B2 | 6/2010 | Ransbury et al. |
| 7,738,958 B2 | 6/2010 | Zdeblick et al. |
| 7,738,964 B2 | 6/2010 | Von Arx et al. |
| 7,742,812 B2 | 6/2010 | Ghanem et al. |
| 7,742,816 B2 | 6/2010 | Masoud et al. |
| 7,742,822 B2 | 6/2010 | Masoud et al. |
| 7,743,151 B2 | 6/2010 | Vallapureddy et al. |
| 7,747,335 B2 | 6/2010 | Williams |
| 7,751,881 B2 | 7/2010 | Cowan et al. |
| 7,758,521 B2 | 7/2010 | Morris et al. |
| 7,761,150 B2 | 7/2010 | Ghanem et al. |
| 7,761,164 B2 | 7/2010 | Verhoef et al. |
| 7,765,001 B2 | 7/2010 | Echt et al. |
| 7,769,452 B2 | 8/2010 | Ghanem et al. |
| 7,783,362 B2 | 8/2010 | Whitehurst et al. |
| 7,792,588 B2 | 9/2010 | Harding |
| 7,797,059 B1 | 9/2010 | Bornzin et al. |
| 7,801,596 B2 | 9/2010 | Fischell et al. |
| 7,809,438 B2 | 10/2010 | Echt et al. |
| 7,840,281 B2 | 11/2010 | Kveen et al. |
| 7,844,331 B2 | 11/2010 | Li et al. |
| 7,844,348 B2 | 11/2010 | Swoyer et al. |
| 7,846,088 B2 | 12/2010 | Ness |
| 7,848,815 B2 | 12/2010 | Brisken et al. |
| 7,848,823 B2 | 12/2010 | Drasler et al. |
| 7,860,455 B2 | 12/2010 | Fukumoto et al. |
| 7,871,433 B2 | 1/2011 | Lattouf |
| 7,877,136 B1 | 1/2011 | Moffitt et al. |
| 7,877,142 B2 | 1/2011 | Moaddeb et al. |
| 7,881,786 B2 | 2/2011 | Jackson |
| 7,881,798 B2 | 2/2011 | Miesel et al. |
| 7,881,810 B1 | 2/2011 | Chitre et al. |
| 7,890,173 B2 | 2/2011 | Brisken et al. |
| 7,890,181 B2 | 2/2011 | Denzene et al. |
| 7,890,192 B1 | 2/2011 | Kelsch et al. |
| 7,894,885 B2 | 2/2011 | Bartal et al. |
| 7,894,894 B2 | 2/2011 | Stadler et al. |
| 7,894,907 B2 | 2/2011 | Cowan et al. |
| 7,894,910 B2 | 2/2011 | Cowan et al. |
| 7,894,915 B1 | 2/2011 | Chitre et al. |
| 7,899,537 B1 | 3/2011 | Kroll et al. |
| 7,899,541 B2 | 3/2011 | Cowan et al. |
| 7,899,542 B2 | 3/2011 | Cowan et al. |
| 7,899,554 B2 | 3/2011 | Williams et al. |
| 7,901,360 B1 | 3/2011 | Yang et al. |
| 7,904,170 B2 | 3/2011 | Harding |
| 7,907,993 B2 | 3/2011 | Ghanem et al. |
| 7,920,928 B1 | 4/2011 | Yang et al. |
| 7,925,343 B1 | 4/2011 | Min et al. |
| 7,930,022 B2 | 4/2011 | Zhang et al. |
| 7,930,040 B1 | 4/2011 | Kelsch et al. |
| 7,937,135 B2 | 5/2011 | Ghanem et al. |
| 7,937,148 B2 | 5/2011 | Jacobson |
| 7,937,161 B2 | 5/2011 | Hastings et al. |
| 7,941,214 B2 | 5/2011 | Kleckner et al. |
| 7,945,333 B2 | 5/2011 | Jacobson |
| 7,946,997 B2 | 5/2011 | Hübinette |
| 7,949,404 B2 | 5/2011 | Hill |
| 7,949,405 B2 | 5/2011 | Feher |
| 7,953,486 B2 | 5/2011 | Daum et al. |
| 7,953,493 B2 | 5/2011 | Fowler et al. |
| 7,962,202 B2 | 6/2011 | Bhunia |
| 7,974,702 B1 | 7/2011 | Fain et al. |
| 7,979,136 B2 | 7/2011 | Young et al. |
| 7,983,753 B2 | 7/2011 | Severin |
| 7,991,467 B2 | 8/2011 | Markowitz et al. |
| 7,991,471 B2 | 8/2011 | Ghanem et al. |
| 7,996,087 B2 | 8/2011 | Cowan et al. |

(56) References Cited

U.S. PATENT DOCUMENTS

| | | |
|---|---|---|
| 8,000,791 B2 | 8/2011 | Sunagawa et al. |
| 8,000,807 B2 | 8/2011 | Morris et al. |
| 8,001,975 B2 | 8/2011 | DiSilvestro et al. |
| 8,002,700 B2 | 8/2011 | Ferek-Petric et al. |
| 8,010,209 B2 | 8/2011 | Jacobson |
| 8,019,419 B1 | 9/2011 | Panescu et al. |
| 8,019,434 B2 | 9/2011 | Quiles et al. |
| 8,027,727 B2 | 9/2011 | Freeberg |
| 8,027,729 B2 | 9/2011 | Sunagawa et al. |
| 8,032,219 B2 | 10/2011 | Neumann et al. |
| 8,036,743 B2 | 10/2011 | Savage et al. |
| 8,046,079 B2 | 10/2011 | Bange et al. |
| 8,046,080 B2 | 10/2011 | Von Arx et al. |
| 8,050,297 B2 | 11/2011 | Delmain et al. |
| 8,050,759 B2 | 11/2011 | Stegemann et al. |
| 8,050,774 B2 | 11/2011 | Kveen et al. |
| 8,055,345 B2 | 11/2011 | Li et al. |
| 8,055,350 B2 | 11/2011 | Roberts |
| 8,060,212 B1 | 11/2011 | Rios et al. |
| 8,065,018 B2 | 11/2011 | Haubrich et al. |
| 8,073,542 B2 | 12/2011 | Doerr |
| 8,078,278 B2 | 12/2011 | Penner |
| 8,078,283 B2 | 12/2011 | Cowan et al. |
| 8,095,123 B2 | 1/2012 | Gray |
| 8,102,789 B2 | 1/2012 | Rosar et al. |
| 8,103,359 B2 | 1/2012 | Reddy |
| 8,103,361 B2 | 1/2012 | Moser |
| 8,112,148 B2 | 2/2012 | Giftakis et al. |
| 8,114,021 B2 | 2/2012 | Robertson et al. |
| 8,121,680 B2 | 2/2012 | Falkenberg et al. |
| 8,123,684 B2 | 2/2012 | Zdeblick |
| 8,126,545 B2 | 2/2012 | Flach et al. |
| 8,131,334 B2 | 3/2012 | Lu et al. |
| 8,140,161 B2 | 3/2012 | Willerton et al. |
| 8,150,521 B2 | 4/2012 | Crowley et al. |
| 8,155,731 B1 | 4/2012 | Bharmi |
| 8,160,672 B2 | 4/2012 | Kim et al. |
| 8,160,702 B2 | 4/2012 | Mann et al. |
| 8,160,704 B2 | 4/2012 | Freeberg |
| 8,165,694 B2 | 4/2012 | Carbanaru et al. |
| 8,175,715 B1 | 5/2012 | Cox |
| 8,180,451 B2 | 5/2012 | Hickman et al. |
| 8,185,213 B2 | 5/2012 | Kveen et al. |
| 8,187,161 B2 | 5/2012 | Li et al. |
| 8,195,293 B2 | 6/2012 | Limousin et al. |
| 8,204,595 B2 | 6/2012 | Pianca et al. |
| 8,204,605 B2 | 6/2012 | Hastings et al. |
| 8,209,014 B2 | 6/2012 | Doerr |
| 8,214,043 B2 | 7/2012 | Matos |
| 8,224,244 B2 | 7/2012 | Kim et al. |
| 8,229,556 B2 | 7/2012 | Li |
| 8,233,985 B2 | 7/2012 | Bulkes et al. |
| 8,251,911 B2 | 8/2012 | MacQuarrie et al. |
| 8,262,578 B1 | 9/2012 | Bharmi et al. |
| 8,265,748 B2 | 9/2012 | Liu et al. |
| 8,265,757 B2 | 9/2012 | Mass et al. |
| 8,280,521 B2 | 10/2012 | Haubrich et al. |
| 8,285,387 B2 | 10/2012 | Utsi et al. |
| 8,290,598 B2 | 10/2012 | Boon et al. |
| 8,290,600 B2 | 10/2012 | Hastings et al. |
| 8,295,939 B2 | 10/2012 | Jacobson |
| 8,301,254 B2 | 10/2012 | Mosesov et al. |
| 8,315,701 B2 | 11/2012 | Cowan et al. |
| 8,315,708 B2 | 11/2012 | Berthelsdorf et al. |
| 8,321,021 B2 | 11/2012 | Kisker et al. |
| 8,321,036 B2 | 11/2012 | Brockway et al. |
| 8,332,036 B2 | 12/2012 | Hastings et al. |
| 8,335,563 B2 | 12/2012 | Stessman |
| 8,335,568 B2 | 12/2012 | Heruth et al. |
| 8,340,750 B2 | 12/2012 | Prakash et al. |
| 8,340,780 B2 | 12/2012 | Hastings et al. |
| 8,352,025 B2 | 1/2013 | Jacobson |
| 8,352,028 B2 | 1/2013 | Wenger |
| 8,352,038 B2 | 1/2013 | Mao et al. |
| 8,359,098 B2 | 1/2013 | Lund et al. |
| 8,364,261 B2 | 1/2013 | Stubbs et al. |
| 8,364,276 B2 | 1/2013 | Willis |
| 8,369,959 B2 | 2/2013 | Meskens |
| 8,369,962 B2 | 2/2013 | Abrahamson |
| 8,380,320 B2 | 2/2013 | Spital |
| 8,386,051 B2 | 2/2013 | Rys |
| 8,391,981 B2 | 3/2013 | Mosesov |
| 8,391,990 B2 | 3/2013 | Smith et al. |
| 8,406,874 B2 | 3/2013 | Liu et al. |
| 8,406,879 B2 | 3/2013 | Shuros et al. |
| 8,406,886 B2 | 3/2013 | Gaunt et al. |
| 8,412,352 B2 | 4/2013 | Griswold et al. |
| 8,417,340 B2 | 4/2013 | Goossen |
| 8,417,341 B2 | 4/2013 | Freeberg |
| 8,423,149 B2 | 4/2013 | Hennig |
| 8,428,722 B2 | 4/2013 | Verhoef et al. |
| 8,433,402 B2 | 4/2013 | Ruben et al. |
| 8,433,409 B2 | 4/2013 | Johnson et al. |
| 8,433,420 B2 | 4/2013 | Bange et al. |
| 8,447,412 B2 | 5/2013 | Dal Molin et al. |
| 8,452,413 B2 | 5/2013 | Young et al. |
| 8,457,740 B2 | 6/2013 | Osche |
| 8,457,742 B2 | 6/2013 | Jacobson |
| 8,457,744 B2 | 6/2013 | Janzig et al. |
| 8,457,761 B2 | 6/2013 | Wariar |
| 8,478,407 B2 | 7/2013 | Demmer et al. |
| 8,478,408 B2 | 7/2013 | Hastings et al. |
| 8,478,431 B2 | 7/2013 | Griswold et al. |
| 8,489,204 B2 * | 7/2013 | Arcot-Krishnamurthy ................. A61B 5/02028 600/508 |
| 8,494,632 B2 | 7/2013 | Sun et al. |
| 8,504,156 B2 | 8/2013 | Bonner et al. |
| 8,509,910 B2 | 8/2013 | Sowder et al. |
| 8,515,559 B2 | 8/2013 | Roberts et al. |
| 8,525,340 B2 | 9/2013 | Eckhardt et al. |
| 8,527,068 B2 | 9/2013 | Ostroff |
| 8,532,790 B2 | 9/2013 | Griswold |
| 8,538,526 B2 | 9/2013 | Stahmann et al. |
| 8,541,131 B2 | 9/2013 | Lund et al. |
| 8,543,205 B2 | 9/2013 | Ostroff |
| 8,547,248 B2 | 10/2013 | Zdeblick et al. |
| 8,548,605 B2 | 10/2013 | Ollivier |
| 8,554,333 B2 | 10/2013 | Wu et al. |
| 8,565,882 B2 | 10/2013 | Matos |
| 8,565,897 B2 | 10/2013 | Regnier et al. |
| 8,571,678 B2 | 10/2013 | Wang |
| 8,577,327 B2 | 11/2013 | Makdissi et al. |
| 8,588,926 B2 | 11/2013 | Moore et al. |
| 8,612,002 B2 | 12/2013 | Faltys et al. |
| 8,615,310 B2 | 12/2013 | Khairkhahan et al. |
| 8,626,280 B2 | 1/2014 | Allavatam et al. |
| 8,626,294 B2 | 1/2014 | Sheldon et al. |
| 8,634,908 B2 | 1/2014 | Cowan |
| 8,634,912 B2 | 1/2014 | Bornzin et al. |
| 8,634,919 B1 | 1/2014 | Hou et al. |
| 8,639,335 B2 | 1/2014 | Peichel et al. |
| 8,644,934 B2 | 2/2014 | Hastings et al. |
| 8,649,859 B2 | 2/2014 | Smith et al. |
| 8,670,842 B1 | 3/2014 | Bornzin et al. |
| 8,676,319 B2 | 3/2014 | Knoll |
| 8,676,335 B2 | 3/2014 | Katoozi et al. |
| 8,700,173 B2 | 4/2014 | Edlund |
| 8,700,181 B2 | 4/2014 | Bornzin et al. |
| 8,705,599 B2 | 4/2014 | dal Molin et al. |
| 8,718,766 B2 | 5/2014 | Wahlberg |
| 8,718,773 B2 | 5/2014 | Willis et al. |
| 8,725,260 B2 | 5/2014 | Shuros et al. |
| 8,738,133 B2 | 5/2014 | Shuros et al. |
| 8,738,147 B2 | 5/2014 | Hastings et al. |
| 8,744,555 B2 | 6/2014 | Allavatam et al. |
| 8,744,572 B1 | 6/2014 | Greenhut et al. |
| 8,747,314 B2 | 6/2014 | Stahmann et al. |
| 8,755,884 B2 | 6/2014 | Demmer et al. |
| 8,758,365 B2 | 6/2014 | Bonner et al. |
| 8,768,483 B2 | 7/2014 | Schmitt et al. |
| 8,774,572 B2 | 7/2014 | Hamamoto |
| 8,781,605 B2 | 7/2014 | Bornzin et al. |
| 8,788,035 B2 | 7/2014 | Jacobson |

(56) References Cited

U.S. PATENT DOCUMENTS

| | | |
|---|---|---|
| 8,788,053 B2 | 7/2014 | Jacobson |
| 8,798,740 B2 | 8/2014 | Samade et al. |
| 8,798,745 B2 | 8/2014 | Jacobson |
| 8,798,762 B2 | 8/2014 | Fain et al. |
| 8,798,770 B2 | 8/2014 | Reddy |
| 8,805,505 B1 | 8/2014 | Roberts |
| 8,805,528 B2 | 8/2014 | Corndorf |
| 8,812,109 B2 | 8/2014 | Blomqvist et al. |
| 8,818,504 B2 | 8/2014 | Bodner et al. |
| 8,827,913 B2 | 9/2014 | Havel et al. |
| 8,831,747 B1 | 9/2014 | Min et al. |
| 8,855,789 B2 | 10/2014 | Jacobson |
| 8,868,186 B2 | 10/2014 | Kroll |
| 8,886,339 B2 | 11/2014 | Faltys et al. |
| 8,903,473 B2 | 12/2014 | Rogers et al. |
| 8,903,500 B2 | 12/2014 | Smith et al. |
| 8,903,513 B2 | 12/2014 | Ollivier |
| 8,909,336 B2 | 12/2014 | Navarro-Paredes et al. |
| 8,914,131 B2 | 12/2014 | Bornzin et al. |
| 8,923,795 B2 | 12/2014 | Makdissi et al. |
| 8,923,963 B2 * | 12/2014 | Bonner ............. A61N 1/3756 607/18 |
| 8,938,300 B2 | 1/2015 | Rosero |
| 8,942,806 B2 | 1/2015 | Sheldon et al. |
| 8,958,892 B2 | 2/2015 | Khairkhahan et al. |
| 8,977,358 B2 | 3/2015 | Ewert et al. |
| 8,989,873 B2 | 3/2015 | Locsin |
| 8,996,109 B2 | 3/2015 | Karst et al. |
| 9,002,467 B2 | 4/2015 | Smith et al. |
| 9,008,776 B2 | 4/2015 | Cowan et al. |
| 9,008,777 B2 | 4/2015 | Dianaty et al. |
| 9,014,818 B2 | 4/2015 | Deterre et al. |
| 9,017,341 B2 | 4/2015 | Bornzin et al. |
| 9,020,611 B2 | 4/2015 | Khairkhahan et al. |
| 9,037,262 B2 | 5/2015 | Regnier et al. |
| 9,042,984 B2 | 5/2015 | Demmer et al. |
| 9,072,911 B2 | 7/2015 | Hastings et al. |
| 9,072,913 B2 | 7/2015 | Jacobson |
| 9,155,882 B2 | 10/2015 | Grubac et al. |
| 9,168,372 B2 | 10/2015 | Fain |
| 9,168,380 B1 | 10/2015 | Greenhut et al. |
| 9,168,383 B2 | 10/2015 | Jacobson et al. |
| 9,180,285 B2 | 11/2015 | Moore et al. |
| 9,192,774 B2 | 11/2015 | Jacobson |
| 9,205,225 B2 | 12/2015 | Khairkhahan et al. |
| 9,216,285 B1 | 12/2015 | Boling et al. |
| 9,216,293 B2 | 12/2015 | Berthiaume et al. |
| 9,216,298 B2 | 12/2015 | Jacobson |
| 9,227,077 B2 | 1/2016 | Jacobson |
| 9,238,145 B2 | 1/2016 | Wenzel et al. |
| 9,242,102 B2 | 1/2016 | Khairkhahan et al. |
| 9,242,113 B2 | 1/2016 | Smith et al. |
| 9,248,300 B2 | 2/2016 | Rys et al. |
| 9,265,436 B2 | 2/2016 | Min et al. |
| 9,265,962 B2 | 2/2016 | Dianaty et al. |
| 9,272,155 B2 | 3/2016 | Ostroff |
| 9,278,218 B2 | 3/2016 | Karst et al. |
| 9,278,229 B1 | 3/2016 | Reinke et al. |
| 9,283,381 B2 | 3/2016 | Grubac et al. |
| 9,283,382 B2 | 3/2016 | Berthiaume et al. |
| 9,289,612 B1 | 3/2016 | Sambelashvili et al. |
| 9,302,115 B2 | 4/2016 | Molin et al. |
| 9,333,364 B2 | 5/2016 | Echt et al. |
| 9,358,387 B2 | 6/2016 | Suwito et al. |
| 9,358,400 B2 | 6/2016 | Jacobson |
| 9,364,675 B2 | 6/2016 | Deterre et al. |
| 9,370,663 B2 | 6/2016 | Moulder |
| 9,375,580 B2 | 6/2016 | Bonner et al. |
| 9,375,581 B2 | 6/2016 | Baru et al. |
| 9,381,365 B2 | 7/2016 | Kibler et al. |
| 9,393,424 B2 | 7/2016 | Demmer et al. |
| 9,393,436 B2 | 7/2016 | Doerr |
| 9,399,139 B2 | 7/2016 | Demmer et al. |
| 9,399,140 B2 | 7/2016 | Cho et al. |
| 9,409,033 B2 | 8/2016 | Jacobson |
| 9,427,594 B1 | 8/2016 | Bornzin et al. |
| 9,433,368 B2 | 9/2016 | Stahmann et al. |
| 9,433,780 B2 | 9/2016 | Régnier et al. |
| 9,492,668 B2 | 11/2016 | Sheldon et al. |
| 9,492,669 B2 | 11/2016 | Demmer et al. |
| 9,492,674 B2 | 11/2016 | Schmidt et al. |
| 9,492,677 B2 | 11/2016 | Greenhut et al. |
| 9,502,754 B2 * | 11/2016 | Zhao ................. A61B 5/00 |
| 9,511,233 B2 | 12/2016 | Sambelashvili |
| 9,511,236 B2 | 12/2016 | Varady et al. |
| 9,511,237 B2 | 12/2016 | Deterre et al. |
| 2002/0032470 A1 | 3/2002 | Linberg |
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035380 A1 | 3/2002 | Rissmann et al. |
| 2002/0035381 A1 | 3/2002 | Bardy et al. |
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049475 A1 | 4/2002 | Bardy et al. |
| 2002/0052636 A1 | 5/2002 | Bardy et al. |
| 2002/0068958 A1 | 6/2002 | Bardy et al. |
| 2002/0072773 A1 | 6/2002 | Bardy et al. |
| 2002/0082665 A1 | 6/2002 | Haller et al. |
| 2002/0091414 A1 | 7/2002 | Bardy et al. |
| 2002/0095196 A1 | 7/2002 | Linberg |
| 2002/0099423 A1 | 7/2002 | Berg et al. |
| 2002/0103510 A1 | 8/2002 | Bardy et al. |
| 2002/0107545 A1 | 8/2002 | Rissmann et al. |
| 2002/0107546 A1 | 8/2002 | Ostroff et al. |
| 2002/0107547 A1 | 8/2002 | Erlinger et al. |
| 2002/0107548 A1 | 8/2002 | Bardy et al. |
| 2002/0107549 A1 | 8/2002 | Bardy et al. |
| 2002/0107559 A1 | 8/2002 | Sanders et al. |
| 2002/0120299 A1 | 8/2002 | Ostroff et al. |
| 2002/0173830 A1 | 11/2002 | Starkweather et al. |
| 2002/0193846 A1 | 12/2002 | Pool et al. |
| 2003/0009203 A1 | 1/2003 | Lebel et al. |
| 2003/0028082 A1 | 2/2003 | Thompson |
| 2003/0040779 A1 | 2/2003 | Engmark et al. |
| 2003/0041866 A1 | 3/2003 | Linberg et al. |
| 2003/0045805 A1 | 3/2003 | Sheldon et al. |
| 2003/0088278 A1 | 5/2003 | Bardy et al. |
| 2003/0097153 A1 | 5/2003 | Bardy et al. |
| 2003/0105497 A1 | 6/2003 | Zhu et al. |
| 2003/0114908 A1 | 6/2003 | Flach |
| 2003/0144701 A1 | 7/2003 | Mehra et al. |
| 2003/0187460 A1 | 10/2003 | Chin et al. |
| 2003/0187461 A1 | 10/2003 | Chin |
| 2004/0024435 A1 | 2/2004 | Leckrone et al. |
| 2004/0068302 A1 | 4/2004 | Rodgers et al. |
| 2004/0087938 A1 | 5/2004 | Leckrone et al. |
| 2004/0088035 A1 | 5/2004 | Guenst et al. |
| 2004/0102830 A1 | 5/2004 | Williams |
| 2004/0127959 A1 | 7/2004 | Amundson et al. |
| 2004/0133242 A1 | 7/2004 | Chapman et al. |
| 2004/0147969 A1 | 7/2004 | Mann et al. |
| 2004/0147973 A1 | 7/2004 | Hauser |
| 2004/0167558 A1 | 8/2004 | Igo et al. |
| 2004/0167587 A1 | 8/2004 | Thompson |
| 2004/0172071 A1 | 9/2004 | Bardy et al. |
| 2004/0172077 A1 | 9/2004 | Chinchoy |
| 2004/0172104 A1 | 9/2004 | Berg et al. |
| 2004/0176817 A1 | 9/2004 | Wahlstrand et al. |
| 2004/0176818 A1 | 9/2004 | Wahlstrand et al. |
| 2004/0176830 A1 | 9/2004 | Fang |
| 2004/0186529 A1 | 9/2004 | Bardy et al. |
| 2004/0204673 A1 | 10/2004 | Flaherty |
| 2004/0210292 A1 | 10/2004 | Bardy et al. |
| 2004/0210293 A1 | 10/2004 | Bardy et al. |
| 2004/0210294 A1 | 10/2004 | Bardy et al. |
| 2004/0215308 A1 | 10/2004 | Bardy et al. |
| 2004/0220624 A1 | 11/2004 | Ritscher et al. |
| 2004/0220626 A1 | 11/2004 | Wagner |
| 2004/0220639 A1 | 11/2004 | Mulligan et al. |
| 2004/0249431 A1 | 12/2004 | Ransbury et al. |
| 2004/0260348 A1 | 12/2004 | Bakken et al. |
| 2004/0267303 A1 | 12/2004 | Guenst |

(56) References Cited

U.S. PATENT DOCUMENTS

| | | |
|---|---|---|
| 2005/0061320 A1 | 3/2005 | Lee et al. |
| 2005/0070962 A1 | 3/2005 | Echt et al. |
| 2005/0102003 A1 | 5/2005 | Grabek et al. |
| 2005/0149138 A1 | 7/2005 | Min et al. |
| 2005/0165466 A1 | 7/2005 | Morris et al. |
| 2005/0182465 A1 | 8/2005 | Ness |
| 2005/0203410 A1 | 9/2005 | Jenkins |
| 2005/0283208 A1 | 12/2005 | Von Arx et al. |
| 2005/0288743 A1 | 12/2005 | Ahn et al. |
| 2006/0042830 A1 | 3/2006 | Maghribi et al. |
| 2006/0052829 A1 | 3/2006 | Sun et al. |
| 2006/0052830 A1 | 3/2006 | Spinelli et al. |
| 2006/0064135 A1 | 3/2006 | Brockway |
| 2006/0064149 A1 | 3/2006 | Belacazar et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0095078 A1 | 5/2006 | Tronnes |
| 2006/0095085 A1 | 5/2006 | Marcus et al. |
| 2006/0106442 A1 | 5/2006 | Richardson et al. |
| 2006/0116746 A1 | 6/2006 | Chin |
| 2006/0135999 A1 | 6/2006 | Bodner et al. |
| 2006/0136004 A1 | 6/2006 | Cowan et al. |
| 2006/0161061 A1 | 7/2006 | Echt et al. |
| 2006/0200002 A1 | 9/2006 | Guenst |
| 2006/0206151 A1 | 9/2006 | Lu |
| 2006/0212079 A1 | 9/2006 | Routh et al. |
| 2006/0241701 A1 | 10/2006 | Markowitz et al. |
| 2006/0241705 A1 | 10/2006 | Neumann et al. |
| 2006/0247672 A1 | 11/2006 | Vidlund et al. |
| 2006/0259088 A1 | 11/2006 | Pastore et al. |
| 2006/0265018 A1 | 11/2006 | Smith et al. |
| 2007/0004979 A1 | 1/2007 | Wojciechowicz et al. |
| 2007/0016098 A1 | 1/2007 | Kim et al. |
| 2007/0027508 A1 | 2/2007 | Cowan |
| 2007/0078490 A1 | 4/2007 | Cowan et al. |
| 2007/0088394 A1 | 4/2007 | Jacobson |
| 2007/0088396 A1 | 4/2007 | Jacobson |
| 2007/0088397 A1 | 4/2007 | Jacobson |
| 2007/0088398 A1 | 4/2007 | Jacobson |
| 2007/0088405 A1 | 4/2007 | Jacobson |
| 2007/0135882 A1 | 6/2007 | Drasler et al. |
| 2007/0135883 A1 | 6/2007 | Drasler et al. |
| 2007/0150037 A1 | 6/2007 | Hastings et al. |
| 2007/0150038 A1 | 6/2007 | Hastings et al. |
| 2007/0156190 A1 | 7/2007 | Cinbis |
| 2007/0219525 A1 | 9/2007 | Gelfand et al. |
| 2007/0219590 A1 | 9/2007 | Hastings et al. |
| 2007/0225545 A1 | 9/2007 | Ferrari |
| 2007/0233206 A1 | 10/2007 | Frikart et al. |
| 2007/0239244 A1 | 10/2007 | Morgan et al. |
| 2007/0255376 A1 | 11/2007 | Michels et al. |
| 2007/0276444 A1 | 11/2007 | Gelbart et al. |
| 2007/0293900 A1 | 12/2007 | Sheldon et al. |
| 2007/0293904 A1 | 12/2007 | Gelbart et al. |
| 2008/0004663 A1 | 1/2008 | Jorgenson |
| 2008/0021505 A1 | 1/2008 | Hastings et al. |
| 2008/0021519 A1 | 1/2008 | De Geest et al. |
| 2008/0021532 A1 | 1/2008 | Kveen et al. |
| 2008/0065183 A1 | 3/2008 | Whitehurst et al. |
| 2008/0065185 A1 | 3/2008 | Worley |
| 2008/0071318 A1 | 3/2008 | Brooke et al. |
| 2008/0109054 A1 | 5/2008 | Hastings et al. |
| 2008/0119911 A1 | 5/2008 | Rosero |
| 2008/0130670 A1 | 6/2008 | Kim et al. |
| 2008/0154139 A1 | 6/2008 | Shuros et al. |
| 2008/0154322 A1 | 6/2008 | Jackson et al. |
| 2008/0228234 A1 | 9/2008 | Stancer |
| 2008/0234771 A1 | 9/2008 | Chinchoy et al. |
| 2008/0243217 A1 | 10/2008 | Wildon |
| 2008/0269814 A1 | 10/2008 | Rosero |
| 2008/0269825 A1 | 10/2008 | Chinchoy et al. |
| 2008/0275518 A1 | 11/2008 | Ghanem et al. |
| 2008/0275519 A1 | 11/2008 | Ghanem et al. |
| 2008/0288039 A1 | 11/2008 | Reddy |
| 2008/0294208 A1 | 11/2008 | Willis et al. |
| 2008/0294210 A1 | 11/2008 | Rosero |
| 2008/0306359 A1 | 12/2008 | Zdeblick et al. |
| 2009/0018599 A1 | 1/2009 | Hastings et al. |
| 2009/0024180 A1 | 1/2009 | Kisker et al. |
| 2009/0036941 A1 | 2/2009 | Corbucci |
| 2009/0048646 A1 | 2/2009 | Katoozi et al. |
| 2009/0062895 A1 | 3/2009 | Stahmann et al. |
| 2009/0082827 A1 | 3/2009 | Kveen et al. |
| 2009/0082828 A1 | 3/2009 | Ostroff |
| 2009/0088813 A1 | 4/2009 | Brockway et al. |
| 2009/0131907 A1 | 5/2009 | Chin et al. |
| 2009/0135886 A1 | 5/2009 | Robertson et al. |
| 2009/0143835 A1 | 6/2009 | Pastore et al. |
| 2009/0171408 A1 | 7/2009 | Solem |
| 2009/0171414 A1 | 7/2009 | Kelly et al. |
| 2009/0204163 A1 | 8/2009 | Shuros et al. |
| 2009/0204170 A1 | 8/2009 | Hastings et al. |
| 2009/0210024 A1 | 8/2009 | M |
| 2009/0216292 A1 | 8/2009 | Pless et al. |
| 2009/0234407 A1 | 9/2009 | Hastings et al. |
| 2009/0234411 A1 | 9/2009 | Sambelashvili et al. |
| 2009/0266573 A1 | 10/2009 | Engmark et al. |
| 2009/0275998 A1 | 11/2009 | Burnes et al. |
| 2009/0275999 A1 | 11/2009 | Burnes et al. |
| 2009/0299447 A1 | 12/2009 | Jensen et al. |
| 2010/0013668 A1 | 1/2010 | Kantervik |
| 2010/0016911 A1 | 1/2010 | Willis et al. |
| 2010/0023085 A1 | 1/2010 | Wu et al. |
| 2010/0030061 A1 | 2/2010 | Canfield et al. |
| 2010/0030327 A1 | 2/2010 | Chatel |
| 2010/0042108 A1 | 2/2010 | Hibino |
| 2010/0056871 A1 | 3/2010 | Govari et al. |
| 2010/0063375 A1 | 3/2010 | Kassab et al. |
| 2010/0063562 A1 | 3/2010 | Cowan et al. |
| 2010/0094367 A1 | 4/2010 | Sen |
| 2010/0114209 A1 | 5/2010 | Krause et al. |
| 2010/0114214 A1 | 5/2010 | Morelli et al. |
| 2010/0125281 A1 | 5/2010 | Jacobson et al. |
| 2010/0168761 A1 | 7/2010 | Kassab et al. |
| 2010/0168819 A1 | 7/2010 | Freeberg |
| 2010/0198288 A1 | 8/2010 | Ostroff |
| 2010/0198304 A1 | 8/2010 | Wang |
| 2010/0217367 A1 | 8/2010 | Belson |
| 2010/0228308 A1 | 9/2010 | Cowan et al. |
| 2010/0234906 A1 | 9/2010 | Koh |
| 2010/0234924 A1 | 9/2010 | Willis |
| 2010/0241185 A1 | 9/2010 | Mahapatra et al. |
| 2010/0249729 A1 | 9/2010 | Morris et al. |
| 2010/0286744 A1 | 11/2010 | Echt et al. |
| 2010/0312309 A1 | 12/2010 | Harding |
| 2011/0022113 A1 | 1/2011 | Zdeblick et al. |
| 2011/0071586 A1 | 3/2011 | Jacobson |
| 2011/0077708 A1 | 3/2011 | Ostroff |
| 2011/0112600 A1 | 5/2011 | Cowan et al. |
| 2011/0118588 A1 | 5/2011 | Komblau et al. |
| 2011/0118810 A1 | 5/2011 | Cowan et al. |
| 2011/0130670 A1 | 6/2011 | MacQuarrie et al. |
| 2011/0137187 A1 | 6/2011 | Yang et al. |
| 2011/0144720 A1 | 6/2011 | Cowan et al. |
| 2011/0152970 A1 | 6/2011 | Jollota et al. |
| 2011/0160558 A1 | 6/2011 | Rassatt et al. |
| 2011/0160565 A1 | 6/2011 | Stubbs et al. |
| 2011/0160801 A1 | 6/2011 | Markowitz et al. |
| 2011/0160806 A1 | 6/2011 | Lyden et al. |
| 2011/0166620 A1 | 7/2011 | Cowan et al. |
| 2011/0166621 A1 | 7/2011 | Cowan et al. |
| 2011/0184491 A1 | 7/2011 | Kivi |
| 2011/0190835 A1 | 8/2011 | Brockway et al. |
| 2011/0208260 A1 | 8/2011 | Jacobson |
| 2011/0218587 A1 | 9/2011 | Jacobson |
| 2011/0230734 A1 | 9/2011 | Fain et al. |
| 2011/0237967 A1 | 9/2011 | Moore et al. |
| 2011/0245890 A1 | 10/2011 | Brisben et al. |
| 2011/0251660 A1 | 10/2011 | Griswold |
| 2011/0251662 A1 | 10/2011 | Griswold et al. |
| 2011/0270099 A1 | 11/2011 | Ruben et al. |
| 2011/0270339 A1 | 11/2011 | Murray, III et al. |
| 2011/0270340 A1 | 11/2011 | Pellegrini et al. |

(56) References Cited

U.S. PATENT DOCUMENTS

| | | |
|---|---|---|
| 2011/0276102 A1 | 11/2011 | Cohen |
| 2011/0282423 A1 | 11/2011 | Jacobson |
| 2012/0004527 A1 | 1/2012 | Thompson et al. |
| 2012/0029323 A1 | 2/2012 | Zhao |
| 2012/0041508 A1 | 2/2012 | Rousso et al. |
| 2012/0059433 A1 | 3/2012 | Cowan et al. |
| 2012/0059436 A1 | 3/2012 | Fontaine et al. |
| 2012/0065500 A1 | 3/2012 | Rogers et al. |
| 2012/0078322 A1 | 3/2012 | Dal Molin et al. |
| 2012/0089198 A1 | 4/2012 | Ostroff |
| 2012/0093245 A1 | 4/2012 | Makdissi et al. |
| 2012/0095521 A1 | 4/2012 | Hintz |
| 2012/0095539 A1 | 4/2012 | Khairkhahan et al. |
| 2012/0101540 A1 | 4/2012 | O'Brien et al. |
| 2012/0101553 A1 | 4/2012 | Reddy |
| 2012/0109148 A1 | 5/2012 | Bonner et al. |
| 2012/0109149 A1 | 5/2012 | Bonner et al. |
| 2012/0109236 A1 | 5/2012 | Jacobson et al. |
| 2012/0109259 A1 | 5/2012 | Bond et al. |
| 2012/0116489 A1 | 5/2012 | Khairkhahan et al. |
| 2012/0150251 A1 | 6/2012 | Giftakis et al. |
| 2012/0158111 A1 | 6/2012 | Khairkhahan et al. |
| 2012/0165827 A1 | 6/2012 | Khairkhahan et al. |
| 2012/0172690 A1 | 7/2012 | Anderson et al. |
| 2012/0172891 A1 | 7/2012 | Lee |
| 2012/0172892 A1 | 7/2012 | Grubac et al. |
| 2012/0172942 A1 | 7/2012 | Berg |
| 2012/0194341 A1 | 8/2012 | Peichel et al. |
| 2012/0197350 A1 | 8/2012 | Roberts et al. |
| 2012/0197373 A1 | 8/2012 | Khairkhahan et al. |
| 2012/0215285 A1 | 8/2012 | Tahmasian et al. |
| 2012/0232565 A1 | 9/2012 | Kveen et al. |
| 2012/0277600 A1 | 11/2012 | Greenhut |
| 2012/0277606 A1 | 11/2012 | Ellingson et al. |
| 2012/0283795 A1 | 11/2012 | Stancer et al. |
| 2012/0283807 A1 | 11/2012 | Deterre et al. |
| 2012/0290025 A1 | 11/2012 | Keimel |
| 2012/0296381 A1 | 11/2012 | Matos |
| 2012/0303082 A1 | 11/2012 | Dong et al. |
| 2012/0316613 A1 | 12/2012 | Keefe et al. |
| 2013/0012151 A1 | 1/2013 | Hankins |
| 2013/0023975 A1 | 1/2013 | Locsin |
| 2013/0035748 A1 | 2/2013 | Bonner et al. |
| 2013/0041422 A1 | 2/2013 | Jacobson |
| 2013/0053908 A1 | 2/2013 | Smith et al. |
| 2013/0053915 A1 | 2/2013 | Holmstrom et al. |
| 2013/0053921 A1 | 2/2013 | Bonner et al. |
| 2013/0060298 A1 | 3/2013 | Splett et al. |
| 2013/0066169 A1 | 3/2013 | Rys et al. |
| 2013/0072770 A1 | 3/2013 | Rao et al. |
| 2013/0079798 A1 | 3/2013 | Tran et al. |
| 2013/0079861 A1 | 3/2013 | Reinert et al. |
| 2013/0085350 A1 | 4/2013 | Schugt et al. |
| 2013/0085403 A1 | 4/2013 | Gunderson et al. |
| 2013/0085550 A1 | 4/2013 | Polefko et al. |
| 2013/0096649 A1 | 4/2013 | Martin et al. |
| 2013/0103047 A1 | 4/2013 | Steingisser et al. |
| 2013/0103109 A1 | 4/2013 | Jacobson |
| 2013/0110008 A1 | 5/2013 | Bourget et al. |
| 2013/0110127 A1 | 5/2013 | Bornzin et al. |
| 2013/0110192 A1 | 5/2013 | Tran et al. |
| 2013/0110219 A1 | 5/2013 | Bornzin et al. |
| 2013/0116529 A1 | 5/2013 | Min et al. |
| 2013/0116738 A1 | 5/2013 | Samade et al. |
| 2013/0116740 A1 | 5/2013 | Bornzin et al. |
| 2013/0116741 A1 | 5/2013 | Bornzin et al. |
| 2013/0123872 A1 | 5/2013 | Bornzin et al. |
| 2013/0123875 A1 | 5/2013 | Varady et al. |
| 2013/0131591 A1 | 5/2013 | Berthiaume et al. |
| 2013/0131693 A1 | 5/2013 | Berthiaume et al. |
| 2013/0138006 A1 | 5/2013 | Bornzin et al. |
| 2013/0150695 A1 | 6/2013 | Biela et al. |
| 2013/0150911 A1 | 6/2013 | Perschbacher et al. |
| 2013/0150912 A1 | 6/2013 | Perschbacher et al. |
| 2013/0184776 A1 | 7/2013 | Shuros et al. |
| 2013/0196703 A1 | 8/2013 | Masoud et al. |
| 2013/0197609 A1 | 8/2013 | Moore et al. |
| 2013/0231710 A1 | 9/2013 | Jacobson |
| 2013/0238072 A1 | 9/2013 | Deterre et al. |
| 2013/0238073 A1 | 9/2013 | Makdissi et al. |
| 2013/0245476 A1 | 9/2013 | Takizawa et al. |
| 2013/0253342 A1 | 9/2013 | Griswold et al. |
| 2013/0253343 A1 | 9/2013 | Waldhauser et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |
| 2013/0253347 A1 | 9/2013 | Griswold et al. |
| 2013/0261497 A1 | 10/2013 | Pertijs et al. |
| 2013/0265144 A1 | 10/2013 | Banna et al. |
| 2013/0268042 A1 | 10/2013 | Hastings et al. |
| 2013/0274828 A1 | 10/2013 | Willis |
| 2013/0274847 A1 | 10/2013 | Ostroff |
| 2013/0282070 A1 | 10/2013 | Cowan et al. |
| 2013/0282073 A1 | 10/2013 | Cowan et al. |
| 2013/0296727 A1 | 11/2013 | Sullivan et al. |
| 2013/0303872 A1 | 11/2013 | Taff et al. |
| 2013/0324825 A1 | 12/2013 | Ostroff et al. |
| 2013/0325081 A1 | 12/2013 | Karst et al. |
| 2013/0345770 A1 | 12/2013 | Dianaty et al. |
| 2014/0012344 A1 | 1/2014 | Hastings et al. |
| 2014/0018876 A1 | 1/2014 | Ostroff |
| 2014/0018877 A1 | 1/2014 | Demmer et al. |
| 2014/0031836 A1 | 1/2014 | Ollivier |
| 2014/0039570 A1 | 2/2014 | Carroll et al. |
| 2014/0039591 A1 | 2/2014 | Drasler et al. |
| 2014/0043146 A1 | 2/2014 | Makdissi et al. |
| 2014/0046395 A1 | 2/2014 | Regnier et al. |
| 2014/0046420 A1 | 2/2014 | Moore et al. |
| 2014/0058240 A1 | 2/2014 | Mothilal et al. |
| 2014/0058494 A1 | 2/2014 | Ostroff et al. |
| 2014/0074114 A1 | 3/2014 | Khairkhahan et al. |
| 2014/0074186 A1 | 3/2014 | Faltys et al. |
| 2014/0094891 A1 | 4/2014 | Pare et al. |
| 2014/0100627 A1 | 4/2014 | Min |
| 2014/0107723 A1 | 4/2014 | Hou et al. |
| 2014/0121719 A1 | 5/2014 | Bonner et al. |
| 2014/0121720 A1 | 5/2014 | Bonner et al. |
| 2014/0121722 A1 | 5/2014 | Sheldon et al. |
| 2014/0128935 A1 | 5/2014 | Kumar et al. |
| 2014/0135865 A1 | 5/2014 | Hastings et al. |
| 2014/0142648 A1 | 5/2014 | Smith et al. |
| 2014/0148675 A1 | 5/2014 | Nordstrom et al. |
| 2014/0148815 A1 | 5/2014 | Wenzel et al. |
| 2014/0155950 A1 | 6/2014 | Hastings et al. |
| 2014/0169162 A1 | 6/2014 | Romano et al. |
| 2014/0172060 A1 | 6/2014 | Bornzin et al. |
| 2014/0180306 A1 | 6/2014 | Grubac et al. |
| 2014/0180366 A1 | 6/2014 | Edlund |
| 2014/0207149 A1 | 7/2014 | Hastings et al. |
| 2014/0207210 A1 | 7/2014 | Willis et al. |
| 2014/0214104 A1 | 7/2014 | Greenhut et al. |
| 2014/0222098 A1 | 8/2014 | Baru et al. |
| 2014/0222109 A1 | 8/2014 | Moulder |
| 2014/0228913 A1 | 8/2014 | Molin et al. |
| 2014/0236172 A1 | 8/2014 | Hastings et al. |
| 2014/0243848 A1 | 8/2014 | Auricchio et al. |
| 2014/0255298 A1 | 9/2014 | Cole et al. |
| 2014/0257324 A1 | 9/2014 | Fain |
| 2014/0257422 A1 | 9/2014 | Herken |
| 2014/0257444 A1 | 9/2014 | Cole et al. |
| 2014/0276929 A1 | 9/2014 | Foster et al. |
| 2014/0303704 A1 | 10/2014 | Suwito et al. |
| 2014/0309706 A1 | 10/2014 | Jacobson |
| 2014/0379041 A1 | 12/2014 | Foster |
| 2015/0025612 A1 | 1/2015 | Haasl et al. |
| 2015/0038856 A1 | 2/2015 | Houlton et al. |
| 2015/0039041 A1 | 2/2015 | Smith et al. |
| 2015/0051609 A1 | 2/2015 | Schmidt et al. |
| 2015/0051610 A1 | 2/2015 | Schmidt et al. |
| 2015/0051611 A1 | 2/2015 | Schmidt et al. |
| 2015/0051612 A1 | 2/2015 | Schmidt et al. |
| 2015/0051613 A1 | 2/2015 | Schmidt et al. |
| 2015/0051614 A1 | 2/2015 | Schmidt et al. |
| 2015/0051615 A1 | 2/2015 | Schmidt et al. |

(56) References Cited

U.S. PATENT DOCUMENTS

| | | | |
|---|---|---|---|
| 2015/0051616 A1 | 2/2015 | Haasl et al. |
| 2015/0051682 A1 | 2/2015 | Schmidt et al. |
| 2015/0057520 A1 | 2/2015 | Foster et al. |
| 2015/0057558 A1 | 2/2015 | Stahmann et al. |
| 2015/0057721 A1 | 2/2015 | Stahmann et al. |
| 2015/0088155 A1 | 3/2015 | Stahmann et al. |
| 2015/0105836 A1 | 4/2015 | Bonner et al. |
| 2015/0157861 A1 | 6/2015 | Aghassian |
| 2015/0173655 A1 | 6/2015 | Demmer et al. |
| 2015/0190638 A1 | 7/2015 | Smith et al. |
| 2015/0196756 A1 | 7/2015 | Stahmann et al. |
| 2015/0196757 A1 | 7/2015 | Stahmann et al. |
| 2015/0196758 A1 | 7/2015 | Stahmann et al. |
| 2015/0196769 A1 | 7/2015 | Stahmann et al. |
| 2015/0217119 A1 | 8/2015 | Nikolski et al. |
| 2015/0221898 A1 | 8/2015 | Chi et al. |
| 2015/0224315 A1 | 8/2015 | Stahmann |
| 2015/0224320 A1 | 8/2015 | Stahmann |
| 2015/0258345 A1 | 9/2015 | Smith et al. |
| 2015/0290468 A1 | 10/2015 | Zhang |
| 2015/0297905 A1 | 10/2015 | Greenhut et al. |
| 2015/0297907 A1 | 10/2015 | Zhang |
| 2015/0305637 A1 | 10/2015 | Greenhut et al. |
| 2015/0305638 A1 | 10/2015 | Zhang |
| 2015/0305639 A1 | 10/2015 | Greenhut et al. |
| 2015/0305640 A1 | 10/2015 | Reinke et al. |
| 2015/0305641 A1 | 10/2015 | Stadler et al. |
| 2015/0305642 A1 | 10/2015 | Reinke et al. |
| 2015/0306374 A1 | 10/2015 | Seifert et al. |
| 2015/0306375 A1 | 10/2015 | Marshall et al. |
| 2015/0306406 A1 | 10/2015 | Crutchfield et al. |
| 2015/0306407 A1 | 10/2015 | Crutchfield et al. |
| 2015/0306408 A1 | 10/2015 | Greenhut et al. |
| 2015/0321016 A1 | 11/2015 | O'Brien et al. |
| 2015/0328459 A1 | 11/2015 | Chin et al. |
| 2016/0015322 A1 | 1/2016 | Anderson et al. |
| 2016/0023000 A1 | 1/2016 | Cho et al. |
| 2016/0030757 A1 | 2/2016 | Jacobson |
| 2016/0033177 A1 | 2/2016 | Barot et al. |
| 2016/0121127 A1 | 5/2016 | Klimovitch et al. |
| 2016/0121128 A1 | 5/2016 | Fishler et al. |
| 2016/0121129 A1 | 5/2016 | Persson et al. |
| 2016/0213919 A1 | 7/2016 | Suwito et al. |
| 2016/0213937 A1 | 7/2016 | Reinke et al. |
| 2016/0213939 A1 | 7/2016 | Carney et al. |
| 2016/0228026 A1 | 8/2016 | Jackson |
| 2016/0317825 A1 | 11/2016 | Jacobson |

FOREIGN PATENT DOCUMENTS

| | | |
|---|---|---|
| AU | 2014203793 A1 | 7/2014 |
| CA | 1003904 A1 | 1/1977 |
| CN | 202933393 U | 5/2013 |
| EP | 0362611 A1 | 4/1990 |
| EP | 503823 A2 | 9/1992 |
| EP | 1702648 A2 | 9/2006 |
| EP | 1904166 B1 | 6/2011 |
| EP | 2433675 B1 | 1/2013 |
| EP | 2441491 B1 | 1/2013 |
| EP | 2452721 B1 | 11/2013 |
| EP | 1948296 B1 | 1/2014 |
| EP | 2662113 A3 | 1/2014 |
| EP | 2471452 B1 | 12/2014 |
| EP | 2760541 B1 | 5/2016 |
| EP | 2833966 B1 | 5/2016 |
| JP | 2000051373 A | 2/2000 |
| JP | 2002502640 A | 1/2002 |
| JP | 2004512105 A | 4/2004 |
| JP | 2005508208 A | 3/2005 |
| JP | 2005245215 A | 9/2005 |
| JP | 2008540040 A | 11/2008 |
| JP | 5199867 B2 | 2/2013 |
| WO | 9500202 A1 | 1/1995 |
| WO | 9636134 A1 | 11/1996 |
| WO | 9724981 A2 | 7/1997 |
| WO | 9826840 A1 | 6/1998 |
| WO | 9939767 A1 | 8/1999 |
| WO | 0234330 A2 | 1/2003 |
| WO | 02098282 A2 | 5/2003 |
| WO | 2005000206 A3 | 4/2005 |
| WO | 2005042089 A1 | 5/2005 |
| WO | 2006065394 A1 | 6/2006 |
| WO | 2006086435 A3 | 8/2006 |
| WO | 2006113659 A1 | 10/2006 |
| WO | 2006124833 A2 | 11/2006 |
| WO | 2006124833 A3 | 5/2007 |
| WO | 2007075974 A2 | 7/2007 |
| WO | 2009006531 A1 | 1/2009 |
| WO | 2012054102 A1 | 4/2012 |
| WO | 2013080038 A2 | 6/2013 |
| WO | 2013098644 A3 | 8/2013 |
| WO | 2013184787 A1 | 12/2013 |
| WO | 2014120769 A1 | 8/2014 |

OTHER PUBLICATIONS

Hachisuka et al., "Development and Performance Analysis of an Intra-Body Communication Device," The 12th International Conference on Solid State Sensors, Actuators and Microsystems, vol. 4A1.3, pp. 1722-1725, 2003.

Seyedi et al., "A Survey on Intrabody Communications for Body Area Network Application," IEEE Transactions on Biomedical Engineering, vol. 60(8): 2067-2079, 2013.

Wegmüller, "Intra-Body Communication for Biomedical Sensor Networks," Diss. ETH, No. 17323, 1-173, 2007.

Notification of Transmittal of the International Search Report and the Written Opinion of the International Searching Authority, or the Declaration, dated Jan. 29, 2016, 15 pages.

Spickler et al., "Totally Self-Contained Intracardiac Pacemaker," Journal of Electrocardiology, vol. 3(3&4): 324-331, 1970.

"Instructions for Use System 1, Leadless Cardiac Pacemaker (LCP) and Delivery Catheter," Nanostim Leadless Pacemakers, pp. 1-28, 2013.

* cited by examiner

SYSTEMS AND METHODS FOR INFARCT DETECTION

CROSS REFERENCE TO RELATED APPLICATIONS

This application claims the benefit of U.S. Provisional Patent Application Ser. No. 62/211,397 filed on Aug. 28, 2015, the disclosure of which is incorporated herein by reference.

TECHNICAL FIELD

The present disclosure generally relates to systems, devices, and methods for detecting myocardial infarctions, and more particularly, to systems, devices, and methods for detecting myocardial infarctions using an implantable medical device such as a leadless cardiac pacemaker.

BACKGROUND

Pacing instruments can be used to treat patients suffering from various heart conditions that often result in a reduced ability of the heart to deliver sufficient amounts of blood to a patient's body. These heart conditions may lead to rapid, irregular, and/or inefficient heart contractions. To help alleviate some of these conditions, various devices (e.g., pacemakers, defibrillators, etc.) have been implanted in a patient's body. Such devices may monitor and provide electrical stimulation to the heart to help the heart operate in a more normal, efficient and/or safe manner. In some cases, blood flow to a patient's heart may be reduced or cut off, resulting in a myocardial infarction (MI). A MI can lead to a reduced ability of the heart to pump blood, and in some cases can result in serious consequences including death. It may be beneficial for an implanted device to detect occurrences of MIs in order to alert the patient and/or doctor in order to receive or alter treatment.

SUMMARY

The present disclosure generally relates to systems, devices, and methods for detecting myocardial infarctions, and more particularly, to systems, devices, and methods for detecting myocardial infarctions using an implantable medical device such as a leadless cardiac pacemaker.

In a first illustrative embodiment, a method of sensing for an occurrence of a myocardial infarction in a patient's heart using a leadless cardiac pacemaker that is affixed to the patient's heart may comprise sensing, by the leadless cardiac pacemaker, a baseline accelerometer signal generated via an patient accelerometer of the leadless cardiac pacemaker during a baseline period that reflects movement of the patient's heart during the baseline period, determining a baseline template based on one or more characteristics of the baseline accelerometer signal, and storing the baseline template in a memory. The method may further include sensing, by the leadless cardiac pacemaker, an accelerometer signal generated via the accelerometer during a test period subsequent to the baseline period that reflects movement of the patient's heart during the test period, determining a test template based on one or more characteristics of the accelerometer signal during the test period, and comparing the baseline template with the test template, and based on the comparison, determining if a myocardial infarction occurred in the patient's heart. If it is determined that a myocardial infarction has occurred in the patient's heart, the method may further include displaying an indication on a display that a myocardial infarction has occurred in the patient's heart.

Additionally, or alternatively, in the first illustrative embodiment, the method may further comprise transmitting an output signal for reception by a device external to the patient indicating that a myocardial infarction occurred in the patient's heart.

Additionally, or alternatively, in the first illustrative embodiment, the method may further comprise sensing, by the leadless cardiac pacemaker, a cardiac electrical signal during the baseline period, and correlating one or more features of the sensed cardiac electrical signal with one or more features of the accelerometer signal sensed during the baseline period.

Additionally, or alternatively, in the first illustrative embodiment, the method may further comprise sensing, by the leadless cardiac pacemaker, a cardiac electrical signal during the test period, and correlating one or more features of the sensed cardiac electrical signal with one or more features of the accelerometer signal sensed during the test period, and determining that a myocardial infarction has occurred based on differences in the correlation between the cardiac electrical signal and the accelerometer signals sensed during the baseline period and the test period.

Additionally, or alternatively, in any of the above embodiments with respect to the first illustrative embodiment, the memory may be part of the leadless cardiac pacemaker.

Additionally, or alternatively, in any of the above embodiments with respect to the first illustrative embodiment, the baseline template and the test template may be compared by the leadless cardiac pacemaker.

Additionally, or alternatively, in any of the above embodiments with respect to the first illustrative embodiment, the leadless cardiac pacemaker may determine if a myocardial infarction occurred in the patient's heart.

Additionally, or alternatively, in any of the above embodiments with respect to the first illustrative embodiment, the memory may be part of an external device located external to the patient.

Additionally, or alternatively, in any of the above embodiments with respect to the first illustrative embodiment, the baseline template and the test template may be compared by an external device located external to the patient.

Additionally, or alternatively, in any of the above embodiments with respect to the first illustrative embodiment, an external device located external to the patient may determine if a myocardial infarction occurred in the patient's heart.

Additionally, or alternatively, in any of the above embodiments with respect to the first illustrative embodiment, the indication that a myocardial infarction occurred in the patient's heart may be displayed on a display of an external device located external to the patient.

Additionally, or alternatively, in any of the above embodiments with respect to the first illustrative embodiment, the external device may be a device programmer.

Additionally, or alternatively, in any of the above embodiments with respect to the first illustrative embodiment, the external device may be a cellular telephone.

In a second illustrative embodiment, a method of sensing for an occurrence of a myocardial infarction in a patient's heart using a leadless cardiac pacemaker that is affixed to the patient's heart may comprise sampling, by the leadless cardiac pacemaker, a baseline accelerometer signal generated via an accelerometer of the leadless cardiac pacemaker during a baseline period that reflects movement of the patient's heart during the baseline period and storing in a memory one or more characteristics of the baseline accelerometer signal sensed during the baseline period. The method may further include sampling, by the leadless cardiac pacemaker, an accelerometer signal generated via the accelerometer during a test period subsequent to the baseline period that reflects movement of the patients' heart during the test period and comparing one or more characteristics of the accelerometer signal sampled during the test period with the one or more characteristics of the baseline accelerometer signal sampled during the baseline period, and based on the comparison, determining if a myocardial infarction occurred in the patients' heart. If it is determined that a myocardial infarction has occurred in the patient's heart, the method may further include displaying an indication on a display that a myocardial infarction has occurred in the patient's heart.

Additionally, or alternatively, in the second illustrative embodiment, the memory may be part of the leadless cardiac pacemaker.

Additionally, or alternatively, in any of the above embodiments with respect to the second illustrative embodiment, the one or more characteristics of the accelerometer signal sampled during the test period and the one or more characteristics of the baseline accelerometer signal sampled during the baseline period may be compared by the leadless cardiac pacemaker.

Additionally, or alternatively, in any of the above embodiments with respect to the second illustrative embodiment, the leadless cardiac pacemaker may determine if a myocardial infarction occurred in the patient's heart.

Additionally, or alternatively, in any of the above embodiments with respect to the second illustrative embodiment, an external device located external to the patient may determine if a myocardial infarction occurred in the patient's heart.

Additionally, or alternatively, in any of the above embodiments with respect to the second illustrative embodiment, the indication that a myocardial infarction occurred in the patient's heart may be displayed on a display of an external device located external to the patient.

In a third illustrative embodiment, a leadless cardiac pacemaker (LCP) may comprise a plurality of electrodes, an accelerometer, and a memory. In some instances, the LCP may further include a controller connected to the accelerometer, the plurality of electrodes, and the memory. The controller may be configured to: receive an accelerometer signal from the accelerometer; sample the accelerometer signal during a first period of time; store one or more characteristics of the sampled accelerometer signal in the memory; determine whether one or more predetermined characteristics of the accelerometer signal sampled during a second period of time differs from the stored one or more characteristics by at least a predetermined amount, and based on the result, determining if a myocardial infarction has occurred in the patient's heart; and if it is determined that a myocardial infarction has occurred in the patient's heart, transmitting an output signal for reception by a device external to the patient indicating that a myocardial infarction has occurred in the patient's heart.

Additionally, or alternatively, in the third illustrative embodiment, the one or more characteristics may comprise one or more of: an average amplitude of the accelerometer signal; an integral of the accelerometer signal; and a delay of the accelerometer signal relative to a sensed cardiac electrical signal.

Additionally, or alternatively, in any of the above embodiments with respect to the third illustrative embodiment, the controller may be further configured to determine a patient activity level based at least in part on the received accelerometer signal, determine a heart rate of the patient's heart based on a sensed cardiac electrical signal, and use the patient activity level and heart rate, in addition to whether one or more predetermined characteristics of the accelerometer signal sampled during the second period of time differs from the stored one or more characteristics by at least a predetermined amount, when determining if a myocardial infarction occurred in the patient's heart.

In a fourth illustrative embodiment, a medical device for implantation on or within a heart may comprise a plurality of electrodes, an accelerometer, and a controller connected to the plurality of electrodes and the accelerometer. The controller may be configured to sense a baseline accelerometer signal generated via the accelerometer during a baseline period that reflects movement of the accelerometer during the baseline period, sense an accelerometer signal generated via the accelerometer during a test period subsequent to the baseline period that reflects movement of the accelerometer during the test period, and determine if a myocardial infarction has occurred. If it is determined that a myocardial infarction has occurred, the control may be further configured to cause an indication to be displayed on a display that a myocardial infarction has occurred.

Additionally, or alternatively, in the fourth illustrative embodiment, the medical device may be further configured to determine a baseline template based on one or more characteristics of the sensed baseline accelerometer signal.

Additionally, or alternatively, in the fourth illustrative embodiment, the controller may further be configured to sensing, via the plurality of electrodes, a cardiac electrical signal during the baseline period, and correlate one or more features of the sensed cardiac electrical signal with one or more features of the accelerometer signal sensed during the baseline period.

Additionally, or alternatively, in the fourth illustrative embodiment, the controller may further be configured to sense, via the plurality of electrodes, a cardiac electrical signal during the test period, correlate one or more features of the sensed cardiac electrical signal with one or more features of the accelerometer signal sensed during the test period, and determine that a myocardial infarction has occurred based on differences in the correlation between the cardiac electrical signal and the accelerometer signals sensed during the baseline period and the test period.

Additionally, or alternatively, in any of the above embodiments with respect to the fourth illustrative embodiment, the medical device may be further configured to determine a test template based on one or more characteristics of the accelerometer signal sensed during the test period.

Additionally, or alternatively, in any of the above embodiments with respect to the fourth illustrative embodiment, the controller may be further configured to store one or more determined templates in a memory of the medical device.

Additionally, or alternatively, in any of the above embodiments with respect to the fourth illustrative embodiment, the controller may be configured to determine if a myocardial infarction has occurred based on the sensed baseline accelerometer signal and the accelerometer signal sensed during the test period.

Additionally, or alternatively, in any of the above embodiments with respect to the fourth illustrative embodiment, the controller may be configured to determine if a myocardial infarction has occurred based on a comparison between the baseline template and the test template.

Additionally, or alternatively, in any of the above embodiments with respect to the fourth illustrative embodiment, to determine if a myocardial infarction has occurred, the controller may be configured to receive an indication that a myocardial infarction has occurred from a device external to the medical device.

Additionally, or alternatively, in any of the above embodiments with respect to the fourth illustrative embodiment, the controller may be further configured to transmit the sensed baseline accelerometer signal and the sensed test accelerometer signal to a device external to the medical device.

Additionally, or alternatively, in any of the above embodiments with respect to the fourth illustrative embodiment, the controller may be further configured to determine a baseline template based on one or more characteristics of the baseline accelerometer signal, determine a test template based on one or more characteristics of the accelerometer signal during the test period, and transmit the determine baseline template and the determined test template to a device external to the medical device.

Additionally, or alternatively, in any of the above embodiments with respect to the fourth illustrative embodiment, the controller may be further configured to transmit an output signal for reception by a device external to the medical device to cause the device external to the medical device to display an indication that a myocardial infarction has occurred.

Additionally, or alternatively, in any of the above embodiments with respect to the fourth illustrative embodiment, the medical device may be a leadless cardiac pacemaker.

In a fifth illustrative embodiment, a leadless cardiac pacemaker (LCP) may comprise a plurality of electrodes, an accelerometer, a memory, and a controller connected to the accelerometer, the plurality of electrodes, and the memory. In some embodiments, the controller may be configured to receive an accelerometer signal from the accelerometer, sample the accelerometer signal during a first period of time, store one or more characteristics of the sampled accelerometer signal in the memory, and determine whether one or more predetermined characteristics of the accelerometer signal sampled during a second period of time differs from the stored one or more characteristics by at least a predetermined amount, and based on the result, determining if a myocardial infarction has occurred. If it is determined that a myocardial infarction has occurred, the controller may be further configured to transmit an output signal for reception by a device external to the LCP indicating that a myocardial infarction has occurred.

Additionally, or alternatively, in the fourth illustrative embodiment, the one or more characteristics may comprise one or more of an average amplitude of the accelerometer signal, an integral of the accelerometer signal, and a delay of the accelerometer signal relative to a sensed cardiac electrical signal.

Additionally, or alternatively, in any of the above embodiments with respect to the fourth illustrative embodiment, the output signal may cause the external device to display an indication that a myocardial infarction has occurred.

Additionally, or alternatively, in any of the above embodiments with respect to the fourth illustrative embodiment, the controller may be further configured to determine a patient activity level based at least in part on the received accelerometer signal, determine a heart rate of the patient's heart based on a sensed cardiac electrical signal, and use the patient activity level and heart rate, in addition to whether one or more predetermined characteristics of the accelerometer signal sampled during the second period of time differs from the stored one or more characteristics by at least a predetermined amount, when determining if a myocardial infarction occurred in the patient's heart.

The above summary is not intended to describe each embodiment or every implementation of the present disclosure. Advantages and attainments, together with a more complete understanding of the disclosure, will become apparent and appreciated by referring to the following description and claims taken in conjunction with the accompanying drawings.

BRIEF DESCRIPTION OF THE DRAWINGS

The disclosure may be more completely understood in consideration of the following description of various illustrative embodiments in connection with the accompanying drawings, in which.

Figure 1:
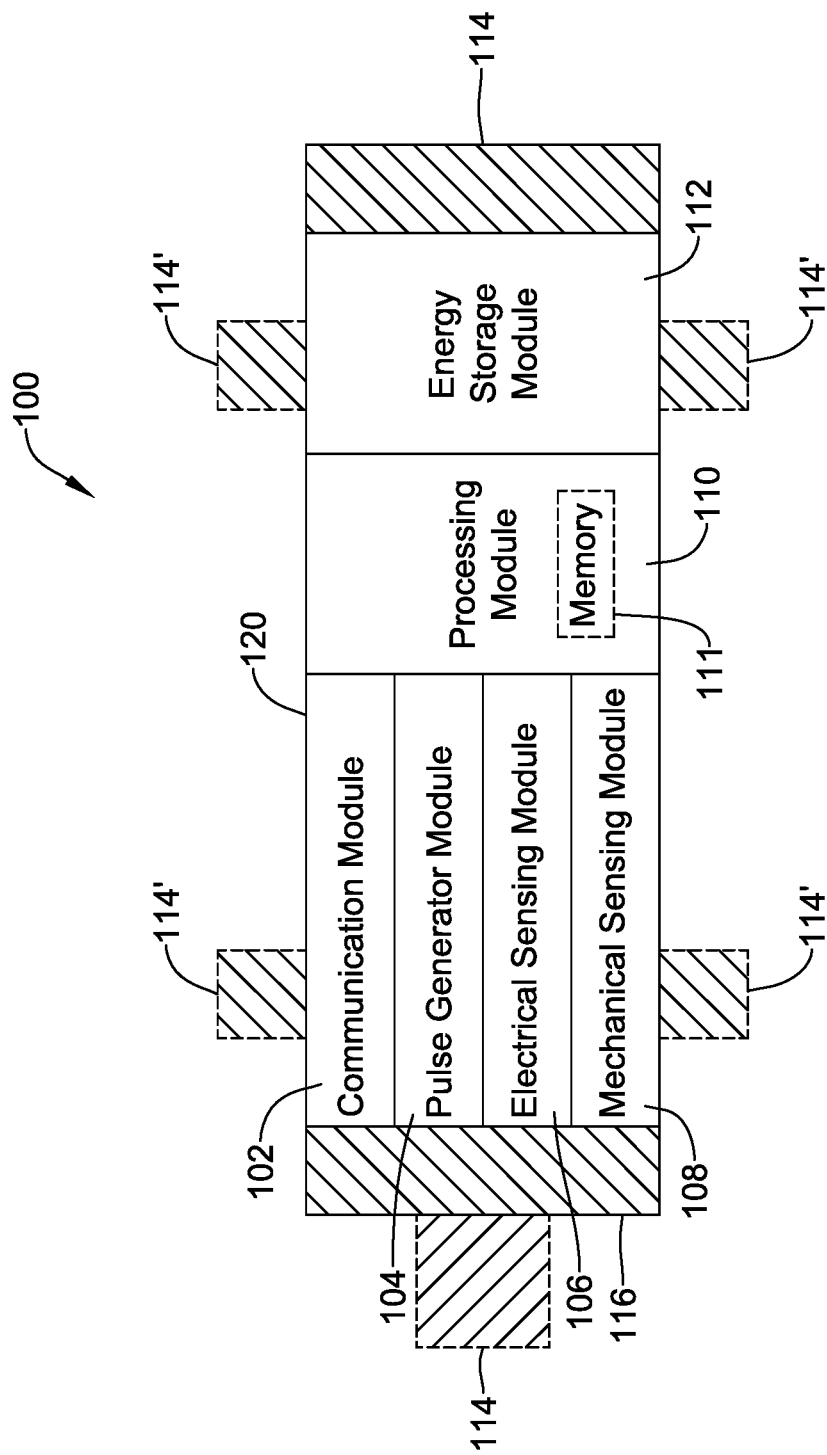
FIG. 1 is a schematic block diagram of an illustrative leadless cardiac pacemaker (LCP) according to one embodiment of the present disclosure.

While the disclosure is amenable to various modifications and alternative forms, specifics thereof have been shown by way of embodiment in the drawings and will be described in detail. It should be understood, however, that the intention is not to limit aspects of the disclosure to the particular illustrative embodiments described. On the contrary, the intention is to cover all modifications, equivalents, and alternatives falling within the spirit and scope of the disclosure.

DESCRIPTION

The following description should be read with reference to the drawings in which similar elements in different drawings are numbered the same. The description and the drawings, which are not necessarily to scale, depict illustrative embodiments and are not intended to limit the scope of the disclosure.

FIG. 1 is a conceptual schematic block diagram of an exemplary leadless cardiac pacemaker (LCP) that may be implanted on the heart or within a chamber of the heart and may operate to sense physiological signals and parameters and deliver one or more types of electrical stimulation therapy to the heart of the patient. Example electrical stimulation therapy may include bradycardia pacing, rate responsive pacing therapy, cardiac resynchronization therapy (CRT), anti-tachycardia pacing (ATP) therapy and/or the like. As can be seen in FIG. 1, LCP 100 may be a compact device with all components housed within LCP 100 or directly on housing 120. In some instances, LCP 100 may include communication module 102, pulse generator module 104, electrical sensing module 106, mechanical sensing module 108, processing module 110, energy storage module 112, and electrodes 114.

As depicted in FIG. 1, LCP 100 may include electrodes 114, which can be secured relative to housing 120 and electrically exposed to tissue and/or blood surrounding LCP 100. Electrodes 114 may generally conduct electrical signals to and from LCP 100 and the surrounding tissue and/or blood. Such electrical signals can include communication signals, electrical stimulation pulses, and intrinsic cardiac electrical signals, to name a few. Intrinsic cardiac electrical signals may include electrical signals generated by the heart and may be represented by an electrocardiogram (ECG).

Electrodes 114 may include one or more biocompatible conductive materials such as various metals or alloys that are known to be safe for implantation within a human body. In some instances, electrodes 114 may be generally disposed on either end of LCP 100 and may be in electrical communication with one or more of modules 102, 104, 106, 108, and 110. In embodiments where electrodes 114 are secured directly to housing 120, an insulative material may electrically isolate the electrodes 114 from adjacent electrodes, housing 120, and/or other parts of LCP 100. In some instances, some or all of electrodes 114 may be spaced from housing 120 and connected to housing 120 and/or other components of LCP 100 through connecting wires. In such instances, the electrodes 114 may be placed on a tail (not shown) that extends out away from the housing 120. As shown in FIG. 1, in some embodiments, LCP 100 may include electrodes 114'. Electrodes 114' may be in addition to electrodes 114, or may replace one or more of electrodes 114. Electrodes 114' may be similar to electrodes 114 except that electrodes 114' are disposed on the sides of LCP 100. In some cases, electrodes 114' may increase the number of electrodes by which LCP 100 may deliver communication signals and/or electrical stimulation pulses, and/or may sense intrinsic cardiac electrical signals, communication signals, and/or electrical stimulation pulses.

Electrodes 114 and/or 114' may assume any of a variety of sizes and/or shapes, and may be spaced at any of a variety of spacings. For example, electrodes 114 may have an outer diameter of two to twenty millimeters (mm). In other embodiments, electrodes 114 and/or 114' may have a diameter of two, three, five, seven millimeters (mm), or any other suitable diameter, dimension and/or shape. Example lengths for electrodes 114 and/or 114' may include, for example, one, three, five, ten millimeters (mm), or any other suitable length. As used herein, the length is a dimension of electrodes 114 and/or 114' that extends away from the outer surface of the housing 120. In some instances, at least some of electrodes 114 and/or 114' may be spaced from one another by a distance of twenty, thirty, forty, fifty millimeters (mm), or any other suitable spacing. The electrodes 114 and/or 114' of a single device may have different sizes with respect to each other, and the spacing and/or lengths of the electrodes on the device may or may not be uniform.

In the embodiment shown, communication module 102 may be electrically coupled to electrodes 114 and/or 114' and may be configured to deliver communication pulses to tissues of the patient for communicating with other devices such as sensors, programmers, other medical devices, and/or the like. Communication signals, as used herein, may be any modulated signal that conveys information to another device, either by itself or in conjunction with one or more other modulated signals. In some embodiments, communication signals may be limited to sub-threshold signals that do not result in capture of the heart yet still convey information. The communication signals may be delivered to another device that is located either external or internal to the patient's body. In some instances, the communication may take the form of distinct communication pulses separated by various amounts of time. In some of these cases, the timing between successive pulses may convey information. Communication module 102 may additionally be configured to sense for communication signals delivered by other devices, which may be located external or internal to the patient's body.

Communication module 102 may communicate to help accomplish one or more desired functions. Some example functions include delivering sensed data, using communicated data for determining occurrences of events such as arrhythmias, coordinating delivery of electrical stimulation therapy, and/or other functions. In some cases, LCP 100 may use communication signals to communicate raw information, processed information, messages and/or commands, and/or other data. Raw information may include information such as sensed electrical signals (e.g. a sensed ECG), signals gathered from coupled sensors, and the like. In some embodiments, the processed information may include signals that have been filtered using one or more signal processing techniques. Processed information may also include parameters and/or events that are determined by the LCP 100 and/or another device, such as a determined heart rate, timing of determined heartbeats, timing of other determined events, determinations of threshold crossings, expirations of monitored time periods, accelerometer signals, activity level parameters, blood-oxygen parameters, blood pressure parameters, heart sound parameters, and the like. Messages and/or commands may include instructions or the like directing another device to take action, notifications of imminent actions of the sending device, requests for reading from the receiving device, requests for writing data to the receiving device, information messages, and/or other messages commands.

In at least some embodiments, communication module 102 (or LCP 100) may further include switching circuitry to selectively connect one or more of electrodes 114 and/or 114' to communication module 102 in order to select which electrodes 114 and/or 114' that communication module 102 delivers communication pulses. It is contemplated that communication module 102 may be communicating with other devices via conducted signals, radio frequency (RF) signals, optical signals, acoustic signals, inductive coupling, and/or any other suitable communication methodology. Where communication module 102 generates electrical communication signals, communication module 102 may include one or more capacitor elements and/or other charge storage devices to aid in generating and delivering communication signals. In the embodiment shown, communication module 102 may use energy stored in energy storage module 112 to generate the communication signals. In at least some examples, communication module 102 may include a switching circuit that is connected to energy storage module 112 and, with the switching circuitry, may connect energy storage module 112 to one or more of electrodes 114/114' to generate the communication signals.

As shown in FIG. 1, a pulse generator module 104 may be electrically connected to one or more of electrodes 114 and/or 114'. Pulse generator module 104 may be configured to generate electrical stimulation pulses and deliver the electrical stimulation pulses to tissues of a patient via one or more of the electrodes 114 and/or 114' in order to effectuate one or more electrical stimulation therapies. Electrical stimulation pulses as used herein are meant to encompass any electrical signals that may be delivered to tissue of a patient for purposes of treatment of any type of disease or abnormality. For example, when used to treat heart disease, the pulse generator module 104 may generate electrical stimulation pacing pulses for capturing the heart of the patient, i.e. causing the heart to contract in response to the delivered electrical stimulation pulse. In some of these cases, LCP 100 may vary the rate at which pulse generator 104 generates the electrical stimulation pulses, for example in rate adaptive pacing. In other embodiments, the electrical stimulation pulses may include defibrillation/cardioversion pulses for shocking the heart out of fibrillation or into a normal heart rhythm. In yet other embodiments, the electrical stimulation pulses may include anti-tachycardia pacing (ATP) pulses. It should be understood that these are just some examples. When used to treat other ailments, the pulse generator module 104 may generate electrical stimulation pulses suitable for neurostimulation therapy or the like. Pulse generator module 104 may include one or more capacitor elements and/or other charge storage devices to aid in generating and delivering appropriate electrical stimulation pulses. In at least some embodiments, pulse generator module 104 may use energy stored in energy storage module 112 to generate the electrical stimulation pulses. In some particular embodiments, pulse generator module 104 may include a switching circuit that is connected to energy storage module 112 and may connect energy storage module 112 to one or more of electrodes 114/114' to generate electrical stimulation pulses.

LCP 100 may further include an electrical sensing module 106 and mechanical sensing module 108. Electrical sensing module 106 may be configured to sense intrinsic cardiac electrical signals conducted from electrodes 114 and/or 114' to electrical sensing module 106. For example, electrical sensing module 106 may be electrically connected to one or more electrodes 114 and/or 114' and electrical sensing module 106 may be configured to receive cardiac electrical signals conducted through electrodes 114 and/or 114' via a sensor amplifier or the like. In some embodiments, the cardiac electrical signals may represent local information from the chamber in which LCP 100 is implanted. For instance, if LCP 100 is implanted within a ventricle of the heart, cardiac electrical signals sensed by LCP 100 through electrodes 114 and/or 114' may represent ventricular cardiac electrical signals. Mechanical sensing module 108 may include, or be electrically connected to, various sensors, such as accelerometers, including multi-axis accelerometers such as two-axis or three-axis accelerometers, gyroscopes, including multi-axis gyroscopes such as two-axis or three-axis gyroscopes, blood pressure sensors, heart sound sensors, piezoelectric sensors, blood-oxygen sensors, and/or other sensors which measure one or more physiological parameters of the heart and/or patient. Mechanical sensing module 108, when present, may gather signals from the sensors indicative of the various physiological parameters. Both electrical sensing module 106 and mechanical sensing module 108 may be connected to processing module 110 and may provide signals representative of the sensed cardiac electrical signals and/or physiological signals to processing module 110. Although described with respect to FIG. 1 as separate sensing modules, in some embodiments, electrical sensing module 106 and mechanical sensing module 108 may be combined into a single module. In at least some examples, LCP 100 may only include one of electrical sensing module 106 and mechanical sensing module 108. In some cases, any combination of the processing module 110, electrical sensing module 106, mechanical sensing module 108, communication module 102, pulse generator module 104 and/or energy storage module may be considered a controller of the LCP 100.

Processing module 110 may be configured to direct the operation of LCP 100 and may, in some embodiments, be termed a controller. For example, processing module 110 may be configured to receive cardiac electrical signals from electrical sensing module 106 and/or physiological signals from mechanical sensing module 108. Based on the received signals, processing module 110 may determine, for example, occurrences and types of arrhythmias and other determinations such as whether LCP 100 has become dislodged. Processing module 110 may further receive information from communication module 102. In some embodiments, processing module 110 may additionally use such received information to determine occurrences and types of arrhythmias and/or and other determinations such as whether LCP 100 has become dislodged. In still some additional embodiments, LCP 100 may use the received information instead of the signals received from electrical sensing module 106 and/or mechanical sensing module 108—for instance if the received information is deemed to be more accurate than the signals received from electrical sensing module 106 and/or mechanical sensing module 108 or if electrical sensing module 106 and/or mechanical sensing module 108 have been disabled or omitted from LCP 100.

After determining an occurrence of an arrhythmia, processing module 110 may control pulse generator module 104 to generate electrical stimulation pulses in accordance with one or more electrical stimulation therapies to treat the determined arrhythmia. For example, processing module 110 may control pulse generator module 104 to generate pacing pulses with varying parameters and in different sequences to effectuate one or more electrical stimulation therapies. As one example, in controlling pulse generator module 104 to deliver bradycardia pacing therapy, processing module 110 may control pulse generator module 104 to deliver pacing pulses designed to capture the heart of the patient at a regular interval to help prevent the heart of a patient from falling below a predetermined threshold. In some cases, the rate of pacing may be increased with an increased activity level of the patient (e.g. rate adaptive pacing). For instance, processing module 110 may monitor one or more physiological parameters of the patient which may indicate a need for an increased heart rate (e.g. due to increased metabolic demand). Processing module 110 may then increase the rate at which pulse generator 104 generates electrical stimulation pulses. Adjusting the rate of delivery of the electrical stimulation pulses based on the one or more physiological parameters may extend the battery life of LCP 100 by only requiring higher rates of delivery of electrical stimulation pulses when the physiological parameters indicate there is a need for increased cardiac output. Additionally, adjusting the rate of delivery of the electrical stimulation pulses may increase a comfort level of the patient by more closely matching the rate of delivery of electrical stimulation pulses with the cardiac output need of the patient.

For ATP therapy, processing module 110 may control pulse generator module 104 to deliver pacing pulses at a rate faster than an intrinsic heart rate of a patient in attempt to force the heart to beat in response to the delivered pacing pulses rather than in response to intrinsic cardiac electrical signals. Once the heart is following the pacing pulses, processing module 110 may control pulse generator module 104 to reduce the rate of delivered pacing pulses down to a safer level. In CRT, processing module 110 may control pulse generator module 104 to deliver pacing pulses in coordination with another device to cause the heart to contract more efficiently. In cases where pulse generator module 104 is capable of generating defibrillation and/or cardioversion pulses for defibrillation/cardioversion therapy, processing module 110 may control pulse generator module 104 to generate such defibrillation and/or cardioversion pulses. In some cases, processing module 110 may control pulse generator module 104 to generate electrical stimulation pulses to provide electrical stimulation therapies different than those examples described above.

Aside from controlling pulse generator module 104 to generate different types of electrical stimulation pulses and in different sequences, in some embodiments, processing module 110 may also control pulse generator module 104 to generate the various electrical stimulation pulses with varying pulse parameters. For example, each electrical stimulation pulse may have a pulse width and a pulse amplitude. Processing module 110 may control pulse generator module 104 to generate the various electrical stimulation pulses with specific pulse widths and pulse amplitudes. For example, processing module 110 may cause pulse generator module 104 to adjust the pulse width and/or the pulse amplitude of electrical stimulation pulses if the electrical stimulation pulses are not effectively capturing the heart. Such control of the specific parameters of the various electrical stimulation pulses may help LCP 100 provide more effective delivery of electrical stimulation therapy.

In some embodiments, processing module 110 may further control communication module 102 to send information to other devices. For example, processing module 110 may control communication module 102 to generate one or more communication signals for communicating with other devices of a system of devices. For instance, processing module 110 may control communication module 102 to generate communication signals in particular pulse sequences, where the specific sequences convey different information. Communication module 102 may also receive communication signals for potential action by processing module 110.

In further embodiments, processing module 110 may control switching circuitry by which communication module 102 and pulse generator module 104 deliver communication signals and/or electrical stimulation pulses to tissue of the patient. As described above, both communication module 102 and pulse generator module 104 may include circuitry for connecting one or more electrodes 114 and/114' to communication module 102 and/or pulse generator module 104 so those modules may deliver the communication signals and electrical stimulation pulses to tissue of the patient. The specific combination of one or more electrodes by which communication module 102 and/or pulse generator module 104 deliver communication signals and electrical stimulation pulses may influence the reception of communication signals and/or the effectiveness of electrical stimulation pulses. Although it was described that each of communication module 102 and pulse generator module 104 may include switching circuitry, in some embodiments, LCP 100 may have a single switching module connected to the communication module 102, the pulse generator module 104, and electrodes 114 and/or 114'. In such embodiments, processing module 110 may control the switching module to connect modules 102/104 and electrodes 114/114' as appropriate.

In some embodiments, processing module 110 may include a pre-programmed chip, such as a very-large-scale integration (VLSI) chip or an application specific integrated circuit (ASIC). In such embodiments, the chip may be pre-programmed with control logic in order to control the operation of LCP 100. By using a pre-programmed chip, processing module 110 may use less power than other programmable circuits while able to maintain basic functionality, thereby potentially increasing the battery life of LCP 100. In other instances, processing module 110 may include a programmable microprocessor or the like. Such a programmable microprocessor may allow a user to adjust the control logic of LCP 100 after manufacture, thereby allowing for greater flexibility of LCP 100 than when using a pre-programmed chip. In still other embodiments, processing module 110 may not be a single component. For example, processing module 110 may include multiple components positioned at disparate locations within LCP 100 in order to perform the various described functions. For example, certain functions may be performed in one component of processing module 110, while other functions are performed in a separate component of processing module 110.

Processing module 110, in additional embodiments, may include a memory circuit 111 and processing module 110 may store information on and read information from the memory circuit 111. In other embodiments, LCP 100 may include a separate memory circuit (not shown) that is in communication with processing module 110, such that processing module 110 may read and write information to and from the separate memory circuit. The memory circuit 111, whether part of processing module 110 (as shown in FIG. 1) or separate from processing module 110, may be volatile memory, non-volatile memory, or a combination of volatile memory and non-volatile memory.

Energy storage module 112 may provide a power source to LCP 100 for its operations. In some embodiments, energy storage module 112 may be a non-rechargeable lithium-based battery. In other embodiments, the non-rechargeable battery may be made from other suitable materials. In some embodiments, energy storage module 112 may include a rechargeable battery. In still other embodiments, energy storage module 112 may include other types of energy storage devices such as capacitors or super capacitors.

To implant LCP 100 inside a patient's body, an operator (e.g., a physician, clinician, etc.), may fix LCP 100 to the cardiac tissue of the patient's heart. To facilitate fixation, LCP 100 may include one or more anchors 116. The one or more anchors 116 are shown schematically in FIG. 1. The one or more anchors 116 may include any number of fixation or anchoring mechanisms. For example, one or more anchors 116 may include one or more pins, staples, threads, screws, helix, tines, and/or the like. In some embodiments, although not shown, one or more anchors 116 may include threads on its external surface that may run along at least a partial length of an anchor member. The threads may provide friction between the cardiac tissue and the anchor to help fix the anchor member within the cardiac tissue. In some cases, the one or more anchors 116 may include an anchor member that has a cork-screw shape that can be screwed into the cardiac tissue. In other embodiments, anchor 116 may include other structures such as barbs, spikes, or the like to facilitate engagement with the surrounding cardiac tissue.

In some examples, LCP 100 may be configured to be implanted on a patient's heart or within a chamber of the patient's heart. For instance, LCP 100 may be implanted within any of a left atrium, right atrium, left ventricle, or right ventricle of a patient's heart. By being implanted within a specific chamber, LCP 100 may be able to sense cardiac electrical signals originating or emanating from the specific chamber that other devices may not be able to sense with such resolution. Where LCP 100 is configured to be implanted on a patient's heart, LCP 100 may be configured to be implanted on or adjacent to one of the chambers of the heart, or on or adjacent to a path along which intrinsically generated cardiac electrical signals generally follow. In these examples, LCP 100 may also have an enhanced ability to sense localized intrinsic cardiac electrical signals and deliver localized electrical stimulation therapy. In embodiments where LCP 100 includes an accelerometer, LCP 100 may additionally be able to sense the motion of the cardiac wall to which LCP 100 is attached.

Figure 2:
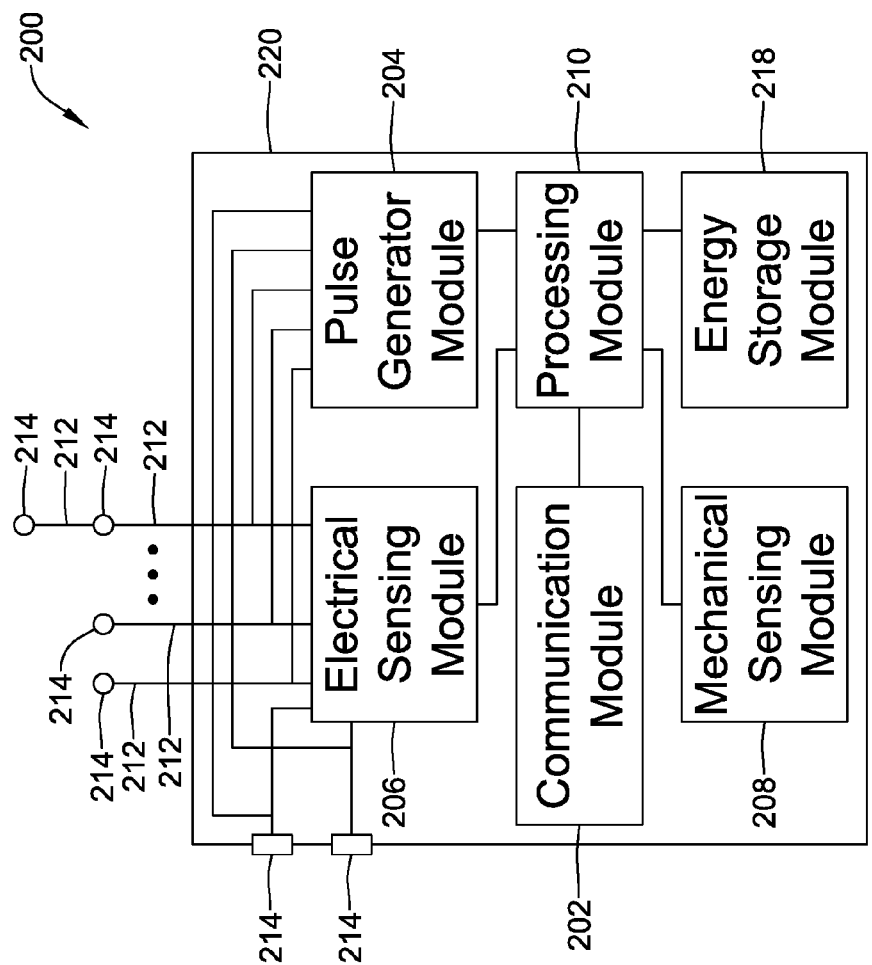
FIG. 2 is a schematic block diagram of another illustrative medical device that may be used in conjunction with the LCP of FIG. 1.

FIG. 2 depicts an embodiment of another device, medical device (MD) 200, which may operate to sense physiological signals and parameters and deliver one or more types of electrical stimulation therapy to tissues of the patient. In the embodiment shown, MD 200 may include a communication module 202, a pulse generator module 204, an electrical sensing module 206, a mechanical sensing module 208, a processing module 210, and an energy storage module 218. Each of modules 202, 204, 206, 208, and 210 may be similar to modules 102, 104, 106, 108, and 110 of LCP 100. Additionally, energy storage module 218 may be similar to energy storage module 112 of LCP 100. However, in some embodiments, MD 200 may have a larger volume within housing 220. In such embodiments, MD 200 may include a larger energy storage module 218 and/or a larger processing module 210 capable of handling more complex operations than processing module 110 of LCP 100.

While MD 200 may be another leadless device such as shown in FIG. 1, in some instances MD 200 may include leads, such as leads 212. Leads 212 may include electrical wires that conduct electrical signals between electrodes 214 and one or more modules located within housing 220. In some cases, leads 212 may be connected to and extend away from housing 220 of MD 200. In some embodiments, leads 212 are implanted on, within, or adjacent to a heart of a patient. Leads 212 may contain one or more electrodes 214 positioned at various locations on leads 212 and various distances from housing 220. Some leads 212 may only include a single electrode 214, while other leads 212 may include multiple electrodes 214. Generally, electrodes 214 are positioned on leads 212 such that when leads 212 are implanted within the patient, one or more of the electrodes 214 are positioned to perform a desired function. In some cases, the one or more of the electrodes 214 may be in contact with the patient's cardiac tissue. In other cases, the one or more of the electrodes 214 may be positioned subcutaneously but adjacent the patient's heart. The electrodes 214 may conduct intrinsically generated electrical cardiac signals to leads 212. Leads 212 may, in turn, conduct the received electrical cardiac signals to one or more of the modules 202, 204, 206, and 208 of MD 200. In some cases, MD 200 may generate electrical stimulation signals, and leads 212 may conduct the generated electrical stimulation signals to electrodes 214. Electrodes 214 may then conduct the electrical stimulation signals to the cardiac tissue of the patient (either directly or indirectly). MD 200 may also include one or more electrodes 214 not disposed on a lead 212. For example, one or more electrodes 214 may be connected directly to housing 220.

Leads 212, in some embodiments, may additionally contain one or more sensors, such as accelerometers, blood pressure sensors, heart sound sensors, blood-oxygen sensors, and/or other sensors which are configured to measure one or more physiological parameters of the heart and/or patient. In such embodiments, mechanical sensing module 208 may be in electrical communication with leads 212 and may receive signals generated from such sensors.

While not required, in some embodiments MD 200 may be an implantable medical device. In such embodiments, housing 220 of MD 200 may be implanted in, for example, a transthoracic region of the patient. Housing 220 may generally include any of a number of known materials that are safe for implantation in a human body and may, when implanted, hermetically seal the various components of MD 200 from fluids and tissues of the patient's body. In such embodiments, leads 212 may be implanted at one or more various locations within the patient, such as within the heart of the patient, adjacent to the heart of the patient, adjacent to the spine of the patient, or any other desired location.

In some embodiments, MD 200 may be an implantable cardiac pacemaker (ICP). In these embodiments, MD 200 may have one or more leads, for example leads 212, which are implanted on or within the patient's heart. The one or more leads 212 may include one or more electrodes 214 that are in contact with cardiac tissue and/or blood of the patient's heart. MD 200 may be configured to sense intrinsically generated cardiac electrical signals and determine, for example, one or more cardiac arrhythmias based on analysis of the sensed signals. MD 200 may be configured to deliver CRT, ATP therapy, bradycardia therapy, and/or other therapy types via leads 212 implanted within the heart. In some embodiments, MD 200 may additionally be configured to provide defibrillation/cardioversion therapy.

In some instances, MD 200 may be an implantable cardioverter-defibrillator (ICD). In such embodiments, MD 200 may include one or more leads implanted within a patient's heart. MD 200 may also be configured to sense electrical cardiac signals, determine occurrences of tachyarrhythmias based on the sensed electrical cardiac signals, and deliver defibrillation and/or cardioversion therapy in response to determining an occurrence of a tachyarrhythmia (for example by delivering defibrillation and/or cardioversion pulses to the heart of the patient). In other embodiments, MD 200 may be a subcutaneous implantable cardioverter-defibrillator (SICD). In embodiments where MD 200 is an SICD, one of leads 212 may be a subcutaneously implanted lead. In at least some embodiments where MD 200 is an SICD, MD 200 may include only a single lead which is implanted subcutaneously but outside of the chest cavity, however this is not required.

In some embodiments, MD 200 may not be an implantable medical device. Rather, MD 200 may be a device external to the patient's body, and electrodes 214 may be skin-electrodes that are placed on a patient's body. In such embodiments, MD 200 may be able to sense surface electrical signals (e.g. electrical cardiac signals that are generated by the heart or electrical signals generated by a device implanted within a patient's body and conducted through the body to the skin). MD 200 may further be configured to deliver various types of electrical stimulation therapy, including, for example, defibrillation therapy via skin-electrodes 214.

Figure 3:
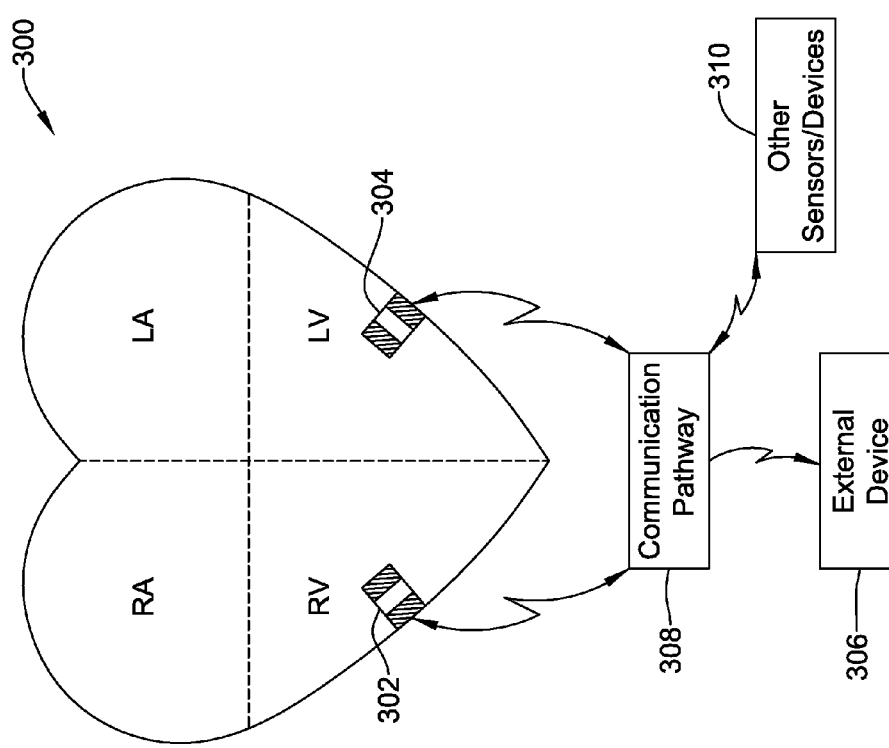
FIG. 3 is a schematic diagram of an exemplary medical system that includes multiple LCPs and/or other devices in communication with one another.

FIG. 3 illustrates an embodiment of a medical device system and a communication pathway through which multiple medical devices 302, 304, 306, and/or 310 of the medical device system may communicate. In the embodiment shown, medical device system 300 may include LCPs 302 and 304, external medical device 306, and other sensors/devices 310. External device 306 may be a device disposed external to a patient's body, as described previously with respect to MD 200. In at least some examples, external device 306 may represent an external support device such as a device programmer, as will be described in more detail below. Other sensors/devices 310 may be any of the devices described previously with respect to MD 200, such as ICPs, ICDs, and SICDs. Other sensors/devices 310 may also include various diagnostic sensors that gather information about the patient, such as accelerometers, blood pressure sensors, or the like. In some cases, other sensors/devices 310 may include an external programmer device that may be used to program one or more devices of system 300.

Various devices of system 300 may communicate via communication pathway 308. For example, LCPs 302 and/or 304 may sense intrinsic cardiac electrical signals and may communicate such signals to one or more other devices 302/304, 306, and 310 of system 300 via communication pathway 308. In one embodiment, one or more of devices 302/304 may receive such signals and, based on the received signals, determine an occurrence of an arrhythmia. In some cases, device or devices 302/304 may communicate such determinations to one or more other devices 306 and 310 of system 300. In some cases, one or more of devices 302/304, 306, and 310 of system 300 may take action based on the communicated determination of an arrhythmia, such as by delivering a suitable electrical stimulation to the heart of the patient. One or more of devices 302/304, 306, and 310 of system 300 may additionally communicate command or response messages via communication pathway 308. The command messages may cause a receiving device to take a particular action whereas response messages may include requested information or a confirmation that a receiving device did, in fact, receive a communicated message or data.

It is contemplated that the various devices of system 300 may communicate via pathway 308 using RF signals, inductive coupling, optical signals, acoustic signals, or any other signals suitable for communication. Additionally, in at least some embodiments, the various devices of system 300 may communicate via pathway 308 using multiple signal types. For instance, other sensors/device 310 may communicate with external device 306 using a first signal type (e.g. RF communication) but communicate with LCPs 302/304 using a second signal type (e.g. conducted communication). Further, in some embodiments, communication between devices may be limited. For instance, as described above, in some embodiments, LCPs 302/304 may communicate with external device 306 only through other sensors/devices 310, where LCPs 302/304 send signals to other sensors/devices 310, and other sensors/devices 310 relay the received signals to external device 306.

In some cases, the various devices of system 300 may communicate via pathway 308 using conducted communication signals. Accordingly, devices of system 300 may have components that allow for such conducted communication. For instance, the devices of system 300 may be configured to transmit conducted communication signals (e.g. a voltage and/or current waveform punctuated with current and/or voltage pulses, referred herein as electrical communication pulses) into the patient's body via one or more electrodes of a transmitting device, and may receive the conducted communication signals via one or more electrodes of a receiving device. The patient's body may "conduct" the conducted communication signals from the one or more electrodes of the transmitting device to the electrodes of the receiving device in the system 300. In such embodiments, the delivered conducted communication signals may differ from pacing pulses, defibrillation and/or cardioversion pulses, or other electrical stimulation therapy signals. For example, the devices of system 300 may deliver electrical communication pulses at an amplitude/pulse width that is sub-threshold. That is, the communication pulses have an amplitude/pulse width designed to not capture the heart. In some cases, the amplitude/pulse width of the delivered electrical communication pulses may be above the capture threshold of the heart, but may be delivered during a refractory period of the heart and/or may be incorporated in or modulated onto a pacing pulse, if desired.

Additionally, unlike normal electrical stimulation therapy pulses, the electrical communication pulses may be delivered in specific sequences which convey information to receiving devices. For instance, delivered electrical communication pulses may be modulated in any suitable manner to encode communicated information. In some cases, the communication pulses may be pulse width modulated and/or amplitude modulated. Alternatively, or in addition, the time between pulses may be modulated to encode desired information. In some cases, a predefined sequence of communication pulses may represent a corresponding symbol (e.g. a logic "1" symbol, a logic "0" symbol, an ATP therapy trigger symbol, etc.). In some cases, conducted communication pulses may be voltage pulses, current pulses, biphasic voltage pulses, biphasic current pulses, or any other suitable electrical pulse as desired.

Figure 4:
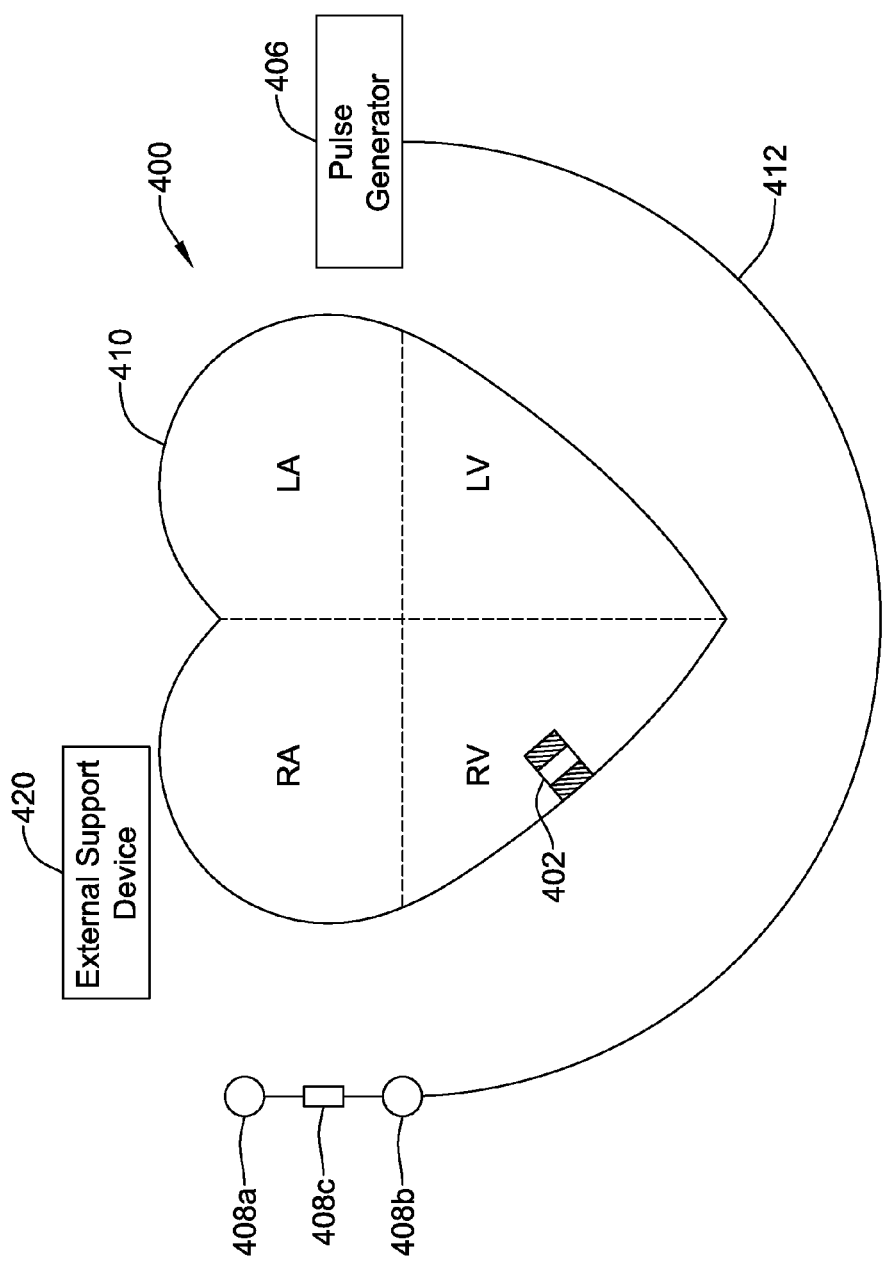
FIG. 4 is a schematic diagram of a system including an LCP and another medical device, in accordance with another embodiment of the present disclosure.

FIG. 4 depicts an illustrative medical device system 400 that may be configured to operate together. For example, system 400 may include multiple devices that are implanted within a patient and are configured to sense physiological signals, determine occurrences of cardiac arrhythmias, and deliver electrical stimulation to treat detected cardiac arrhythmias. In some embodiments, the devices of system 400 may be configured to determine occurrences of dislodgment of one or more devices of system 400. In FIG. 4, an LCP 402 is shown fixed to the interior of the right ventricle of the heart 410, and a pulse generator 406 is shown coupled to a lead 412 having one or more electrodes 408a-408c. In some cases, pulse generator 406 may be part of a subcutaneous implantable cardioverter-defibrillator (SICD), and the one or more electrodes 408a-408c may be positioned subcutaneously adjacent the heart. LCP 402 may communicate with the SICD, such as via communication pathway 308. The locations of LCP 402, pulse generator 406, lead 412, and electrodes 408a-c depicted in FIG. 4 are just exemplary. In other embodiments of system 400, LCP 402 may be positioned in the left ventricle, right atrium, or left atrium of the heart, as desired. In still other embodiments, LCP 402 may be implanted externally adjacent to heart 410 or even remote from heart 410.

Medical device system 400 may also include external support device 420. External support device 420 can be used to perform functions such as device identification, device programming and/or transfer of real-time and/or stored data between devices using one or more of the communication techniques described herein, or other functions involving communication with one or more devices of system 400. As one example, communication between external support device 420 and pulse generator 406 can be performed via a wireless mode, and communication between pulse generator 406 and LCP 402 can be performed via a conducted communication mode. In some embodiments, communication between LCP 402 and external support device 420 is accomplished by sending communication information through pulse generator 406. However, in other embodiments, communication between the LCP 402 and external support device 420 may be via a communication module.

FIG. 4 only illustrates one example embodiment of a medical device system that may be configured to operate according to techniques disclosed herein. Other example medical device systems may include additional or different medical devices and/or configurations. For instance, other medical device systems that are suitable to operate according to techniques disclosed herein may include additional LCPs implanted within the heart. Another example medical device system may include a plurality of LCPs with or without other devices such as pulse generator 406, with at least one LCP capable of delivering defibrillation therapy. Still another example may include one or more LCPs implanted along with a transvenous pacemaker and with or without an implanted SICD. In yet other embodiments, the configuration or placement of the medical devices, leads, and/or electrodes may be different from those depicted in FIG. 4. Accordingly, it should be recognized that numerous other medical device systems, different from system 400 depicted in FIG. 4, may be operated in accordance with techniques disclosed herein. As such, the embodiment shown in FIG. 4 should not be viewed as limiting in any way.

In some embodiments, LCP 100 may be configured to operate in one or more modes. Within each mode, LCP 100 may operate in a somewhat different manner. For instance, in a first mode, LCP 100 may be configured to sense certain signals and/or determine certain parameters. In a second mode, LCP 100 may be configured to sense at least some different signals and/or determine at least some different parameters than in the first mode. In at least one mode, LCP 100 may be configured to determine whether a patient has suffered from a myocardial infarction (MI). For ease of description, a mode that includes LCP 100 being configured to determine whether a patient has suffered from an MI may be called an MI mode. Other modes may include one or more programming and/or therapy modes, and it may be possible for LCP 100 to be engaged in multiple modes concurrently.

When LCP 100 is in an MI mode, LCP 100 may be configured to sense one or more different signals, or one or more signals in a different manner, than when not in an MI mode. As one example, when not in an MI mode, LCP 100 may be configured to sense signals from an accelerometer of mechanical sensing module 108 at first time periods in relation to a cardiac cycle. When in an MI mode, LCP 100 may be configured to sense accelerometer signals at different or additional time periods in relation to a cardiac cycle, or at a higher sampling rate, than when not in an MI mode. In other embodiments, when in an MI mode, LCP 100 may be configured to process sensed signals in a different or additional manner than when not in an MI mode.

When part of a system, LCP 100 may enter an MI mode based on a signal communicated from another device, for example external support device 420 or pulse generator 406. In other embodiments, LCP 100 may be configured to enter an MI mode periodically, intermittently, after a triggering event such as detection of another parameter exceeding a threshold, or the like. In some cases, LCP 100 may be configured to enter an MI mode once an hour, once every six hours, once a day, once every other day, or once a week, or any other suitable time period. In another example, LCP 100 may be configured to enter an MI mode based on one or more characteristics of a sensed signal, as will be described in more detail below.

Throughout this description, LCP 100 is described as sensing signals, determining parameters, and determining whether the patient has suffered from an MI. However, where LCP 100 is part of a system, such as system 400 as one example, the sensing of signals, determining parameters, and determining a whether the patient has suffered from an MI may be split up in any manner between any combinations of the devices of the system. For instance, LCP 100 may sense one or more signals and communicate those signals to another device, such as pulse generator 406. Pulse generator 406, then, may determine one or more parameters and/or and determining whether the patient has suffered from an MI based on the signals received from LCP 100. In other embodiments, pulse generator 406 may determine whether the patient has suffered from an MI on its own, for instance based off of signals sensed by pulse generator 406, and communicate an indication to LCP 100. LCP 100 may then use its own sensed signals to determine whether the patient has suffered from an MI. However, these are only a few examples contemplated by this disclosure of how the sensing, determining, and modulating processes may be split up amongst the devices of a system.

In some embodiments, LCP 100 may include an accelerometer and may be configured to enter an MI mode based on signals received from the accelerometer. For instance, LCP 100 may be configured to sense both cardiac electrical signals and signals generated by the accelerometer. In some instances, the accelerometer may be a three-axis accelerometer, but this is not required. Other contemplated embodiments include accelerometers having one or two axes.

Figure 5:
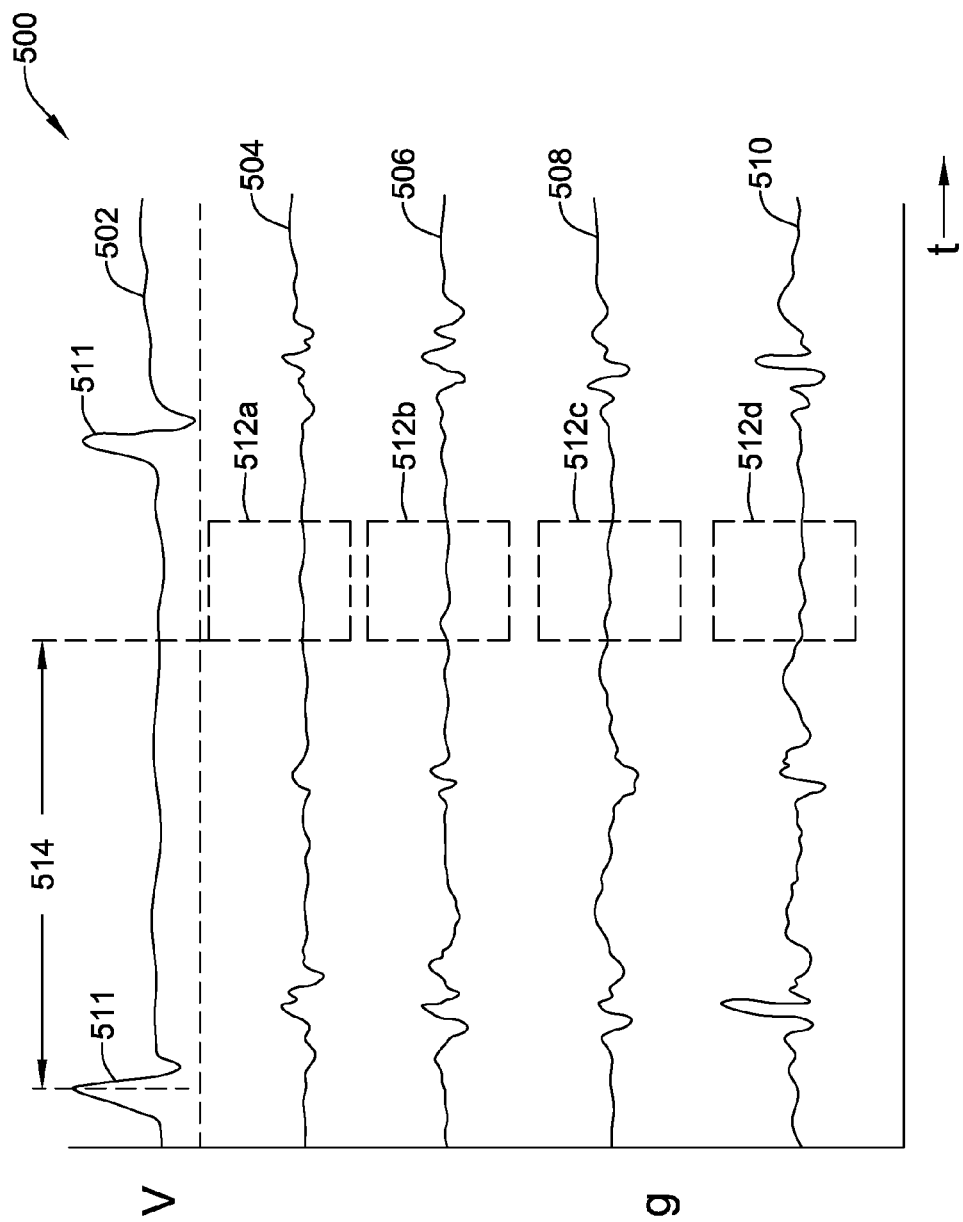
FIG. 5 depicts a graph including a cardiac electrical signal and accelerometer signals tracings shown on the same time axis.

FIG. 5 depicts a graph 500 that includes a number of signal tracings shown on the same time axis. The signal tracings of graph 500 may represent signals sensed or generated by LCP 100 during a time period where LCP 100 is attached to a wall of a patient's heart. In the example shown, signal 502 represents a cardiac electrical signal sensed by LCP 100. Signals 504, 506, and 508 all represent signals from different axes generated by a three-axis accelerometer of LCP 100. Signal 510 represents an accelerometer magnitude signal, which may be determined by summing signals 504, 506, and 508 or summing the absolute values of signals 504, 506, and 508. In other embodiments, signal 510 may represent a different signal generated by another combinations of signals 504, 506, and 508, such as a root-mean-square or root-sum-square of signals 504, 506, and 508, or any other derivation of signals 504, 506, and 508 as desired.

LCP 100 may be configured to sense one or more of signals 504, 506, 508 and/or 510, or generate one or more of signals 504, 506, 508 and/or 510 via the accelerometer, during predetermined time periods. For instance, to sense signals 504, 506, 508 and/or 510, LCP 100 may be configured to receive signals 504, 506, 508 and/or 510 at processing module 110. In some embodiments, LCP 100 may connect an output of the accelerometer to processing module 110 during the time periods where LCP 100 is sensing signals 504, 506, 508 and/or 510. In other embodiments, the accelerometer may be configured to actively output signals 504, 506, 508 and/or 510 during the time periods where LCP 100 is sensing signals 504, 506, 508 and/or 510, for example using a communication link connecting processing module 110. Where processing module 110 is a digital device, sensing signals 504, 506, 508 and/or 510 may be sampled signals 504, 506, 508 and/or 510. In other embodiments, LCP 100 may control the generation of signals 504, 506, 508 and/or 510 by the accelerometer. For instance, LCP 100 may control when power is delivered to the accelerometer, and the accelerometer may only generate signals 504, 506, 508 and/or 510 when power is delivered to the accelerometer, or the accelerometer may only provide a substantial signal at an output during times where power is delivered to the accelerometer. In some cases, LCP 100 may switch the accelerometer from a lower-power state to a higher-power state during time periods where LCP 100 senses the accelerometer signal. During the lower-power state, the accelerometer may not provide an appreciable signal at an output for LCP 100 to sense.

As mentioned, LCP 100 may be configured to sense one or more signals during predetermined time periods. Such predetermined time periods may be represented by sensing periods 512a-512d in FIG. 5. Sensing periods 512a-512d may occur at regular intervals, such as every five seconds, every second, every eight hundred milliseconds, every seven hundred milliseconds, or any other suitable interval. Alternatively, LCP 100 may initiate sensing periods 512a-512d after every beat, once every other beat, once every five beats, or at any other suitable frequency. In at least some cases, LCP 100 may adjust the timing of the intervals according to a heart rate of the patient such that sensing periods 512a-512d occur during the same portion of each successive cardiac cycle.

In some cases, LCP 100 may implement sensing periods 512a-512d based on one or more detected features of cardiac electrical signal 502. For instance, LCP 100 may detect one or more features of cardiac electrical signal 502, such as cardiac electrical events 511. Cardiac electrical events 511 may, in some cases, represent R-waves or other morphological features that may be detected by LCP 100. Upon detection of a cardiac electrical event 511, LCP 100 may initiate a time delay, such as time delay 514. Upon expiration of time delay 514, LCP 100 may initiate sensing periods 512a-512d, during which LCP 100 may sense one or more of signals 504, 506, 508 and 510. In some cases, LCP 100 may adjust time delay 514 based on the heart rate of the patient. For instance, when the heart rate is at a relatively higher rate, LCP 100 may shorten time delay 514, and when the heart rate is at a relatively lower rate, LCP 100 may lengthen time delay 514. This may help to ensure that LCP 100 consistently initiates sensing periods 512a-512d during the same or similar portion of each cardiac cycle.

In some embodiments, the length of time delay 514 may be chosen to align with a portion of the cardiac cycle where the heart is relatively mechanically inactive, such as shown in FIG. 5. For instance, time delay 514 may be chosen so that it expires between about fifty milliseconds to about one-hundred fifty milliseconds before the beginning of a next cardiac electrical event 511. During this portion of the cardiac cycle, the heart muscle may be in a relatively relaxed state while filling with blood. Accordingly, during this portion of the cardiac cycle, the orientation of LCP 100, and hence the accelerometer within LCP 100, may be disposed at relatively consistent position. This may allow LCP 100 to more accurately detect a posture of the patient and/or an activity level of the patient by minimizing movement caused by contraction of the heart.

To determine a posture of the patient, LCP 100 may compare the accelerometer signal captured during a sensing period with a stored template accelerometer signal. For example, LCP 100 may be initially programmed by orienting a patient in a first posture and sensing the accelerometer signal (relative to gravity) during one or more sensing periods while the patient is in the first posture. LCP 100 may store the sensed accelerometer signal in memory. In some cases, this may be repeated several times. In either cases, the LCP may generate an accelerometer signal template. This process may be repeated for different postures. LCP 100 may then compare current sensed accelerometer signals to the stored accelerometer signal templates to determine the current posture of the patient.

In some additional or alternative embodiments, LCP 100 may track a patient activity parameter using the accelerometer signal sensed during the sensing periods 512a-512d. To determine a patient activity parameter, LCP 100 may determine a difference between the sensed or sampled current accelerometer signal and a previously sensed or sampled accelerometer signal. LCP 100 may generate an activity parameter based at least in part on this determined difference. In some cases, LCP 100 may store the determined difference and may generate new determined differences on a rolling basis as LCP 100 sensed or samples new current accelerometer signals. When so provided, LCP 100 may determine a patient activity parameter from multiple of these determined differences. For instance, LCP 100 may sum the differences together over a rolling period of time to produce a patient activity parameter. LCP 100 may then compare the patient activity parameter to one or more thresholds to determine an activity level of the patient.

Figure 6:
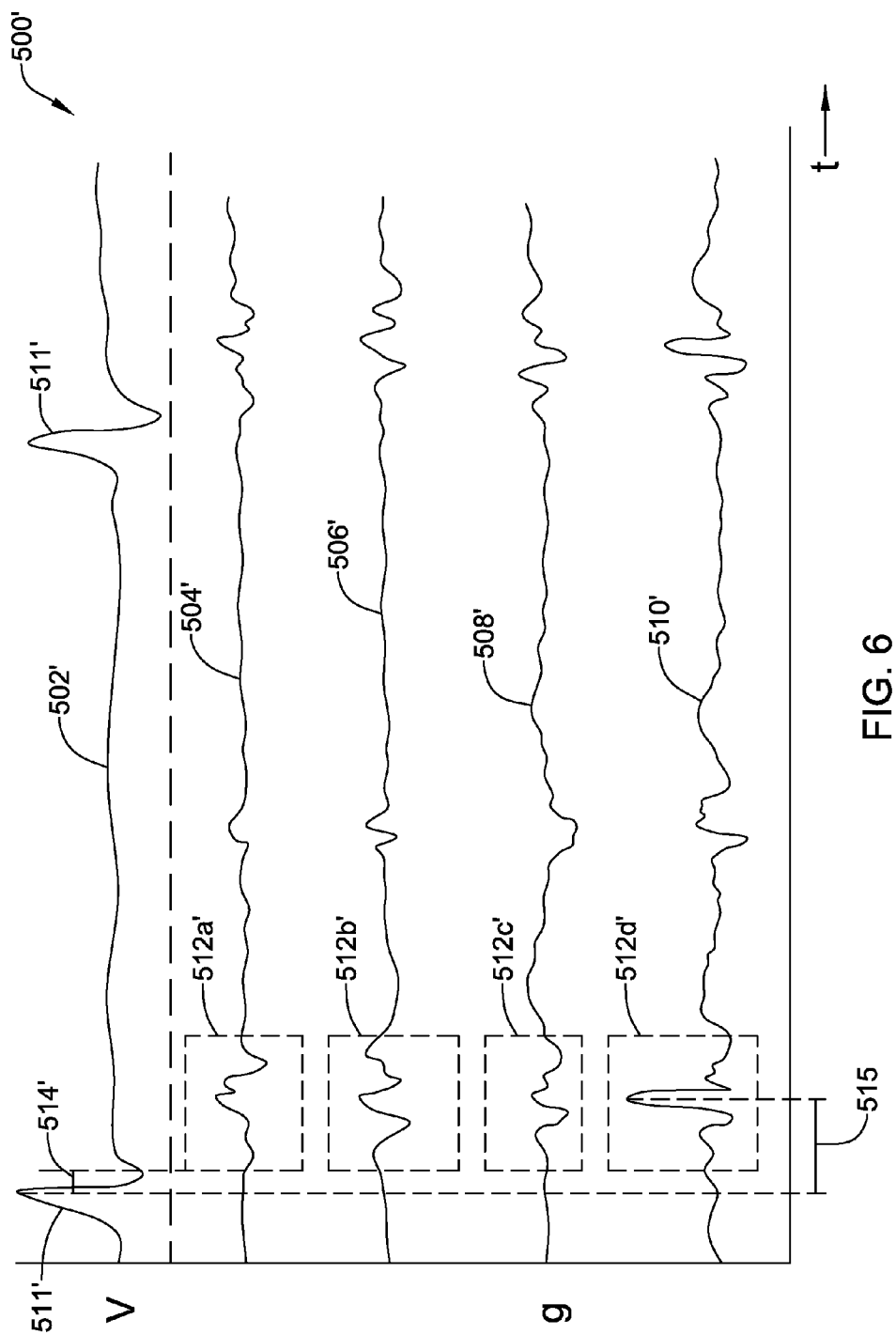
FIG. 6 depicts a graph including a cardiac electrical signal and accelerometer signals tracings shown on the same time axis.

When LCP 100 is in the MI mode, LCP 100 may adjust how LCP 100 senses the accelerometer signal(s). For example, FIG. 6 depicts an example cardiac electrical signal 502', accelerometer signals 504', 506', 508' and 510', and sensing periods 512a'-512d' during which LCP 100 may sense the accelerometer signals. As can be seen, time delay 514' of FIG. 6 is relatively shorter than time delay 514 of FIG. 5. The length of time delay 514' may be chosen to generally align with the contraction of the heart. This may help LCP 100 sense the accelerometer signals during sensing periods 512a'-512d' that correspond to when the heart is actually contracting. Although not shown in FIG. 6, in some cases when in an MI mode, LCP 100 may also sense accelerometer signals 504', 506', 508' and 510' during sensing periods 512a-512d in order to still obtain information related to patient posture and/or activity.

In some instances, time delay 514' may be about ten milliseconds, about fifteen milliseconds, about twenty milliseconds, about twenty-five milliseconds, about thirty milliseconds, about thirty-five milliseconds, or any other suitable period of time following a detected R-wave. In general, time delay 514' may have a value that is less than an electromechanical delay of the heart, which is the delay between when LCP 100 detects a cardiac electrical event 511' (e.g. R-wave) and an onset of cardiac wall motion or a threshold amount of cardiac wall motion. Sensing periods 512a'-512d' may have a duration of about twenty-five milliseconds, about thirty milliseconds, about forty milliseconds, or about fifty milliseconds. However, in other embodiments, sensing periods 512a'-512d' may be substantially longer, for instance, about half of a cardiac cycle of the patient, about three quarters of the cardiac cycle of the patient, or may span an entire cardiac cycle of the patient. In some additional or alternative embodiments, time delay 514' and/or sensing periods 512a'-512d' may have lengths that change along with the heart rate of the patient. As one example, for relatively higher heart rates, time delay 514' and/or sensing periods 512a'-512d' may be shorter than for relatively lower heart rates.

In general, LCP 100 may be able to use accelerometer signals sensed during a portion of the cardiac cycle that corresponds to sensing periods 512a'-512d' to determine whether a patient has suffered from an MI. For example, an MI may cause permanent damage to muscle cells of the heart in one or more localized areas of the heart. Accordingly, an MI may cause a change in the cardiac wall motion of the heart during a contraction. The area or areas of the heart affected by the MI may not contract at all, or may contract at a reduced level, while other areas of the heart may contract more forcefully in an attempt to make up for the damaged portions of the heart. Using an accelerometer, LCP 100, attached to the wall of the heart, may be used to detect these changes.

Figure 7:
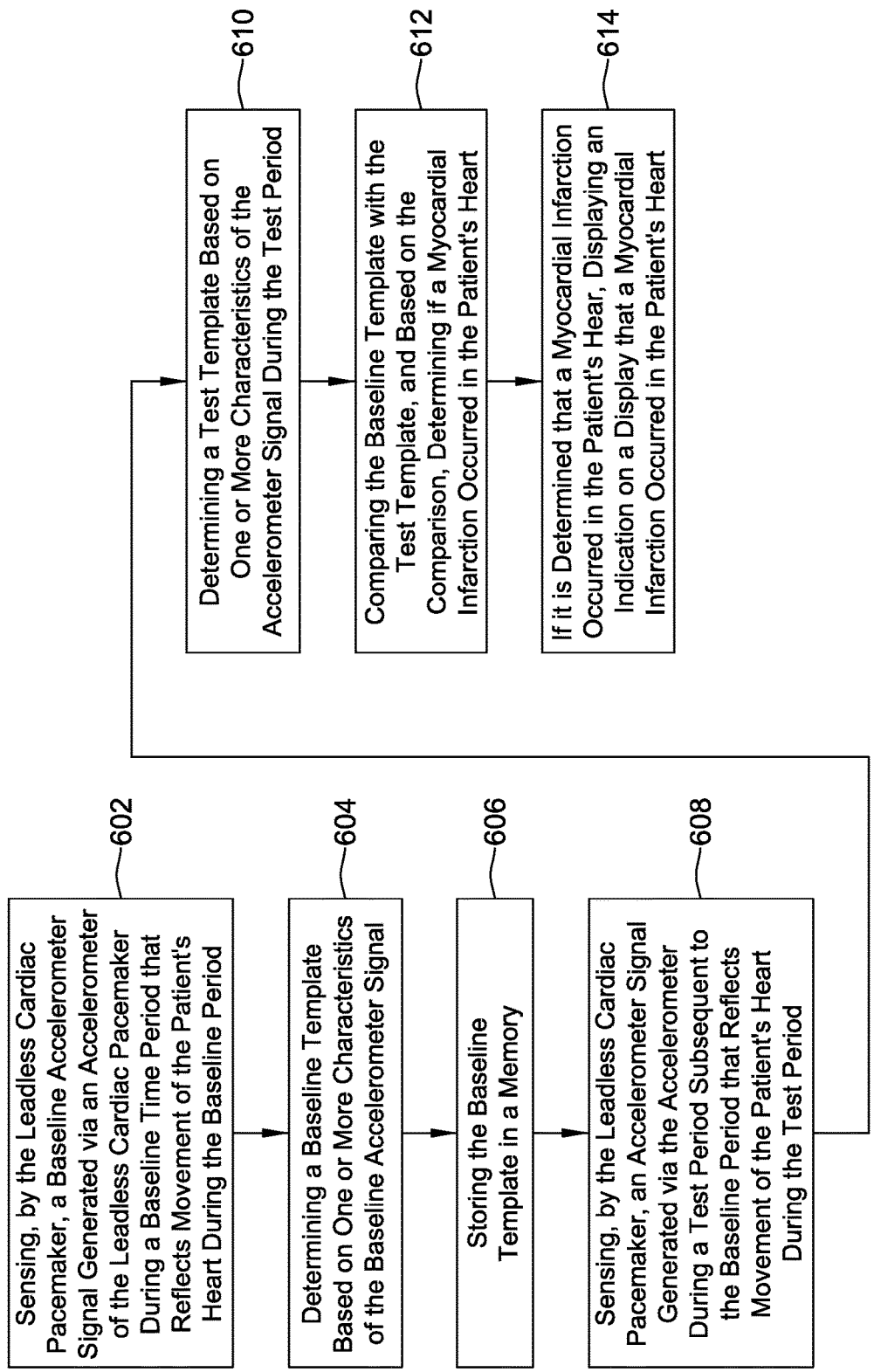
FIG. 7 depicts a method of detecting an occurrence of a myocardial infarction (MI), in accordance with aspects of the present disclosure.

FIG. 7 depicts a flow diagram of an illustrative method 600 of determining whether an MI has occurred. In the example shown, LCP 100 is configured to sense an accelerometer signal generated via an accelerometer of the LCP 100 during a baseline period that reflects movement of the patient's heart during the baseline period, as at 602. The baseline period may be a period where it is known that the patient has not suffered from an MI or has suffered from a known number of MIs. During this baseline period, LCP 100 may sense accelerometer signals during portions of the cardiac cycle corresponding to sensing periods 512a'-512d'. In some additional or alternative embodiments, LCP 100 may also sense one or more cardiac electrical signal during the baseline period.

The method may further include determining a baseline template based on one or more characteristics of the baseline accelerometer signal, as shown at 604. In some embodiments, the baseline template may simply by the accelerometer signals sensed during the sensing periods, resulting in baseline accelerometer signal templates. Where LCP 100 also senses the cardiac electrical signal, the sensed cardiac signal may form a baseline cardiac signal template.

In additional or alternative embodiments, the baseline template may include one or more determined characteristics. For instance, LCP 100 may determine one or more baseline characteristics based on the sensed accelerometer signals and/or the sensed cardiac electrical signal. One example baseline characteristic may include the average amplitude of the sensed accelerometer signal during the sensing period. Another example baseline characteristic may include the maximum amplitude of the sensed accelerometer signal during the sensing period. Additional or alternative baseline characteristics may include the integral of the sensed accelerometer signal during the sensing period, the relative phase of the sensed accelerometer signals, a delay parameter, and/or a vector map.

Figure 10:
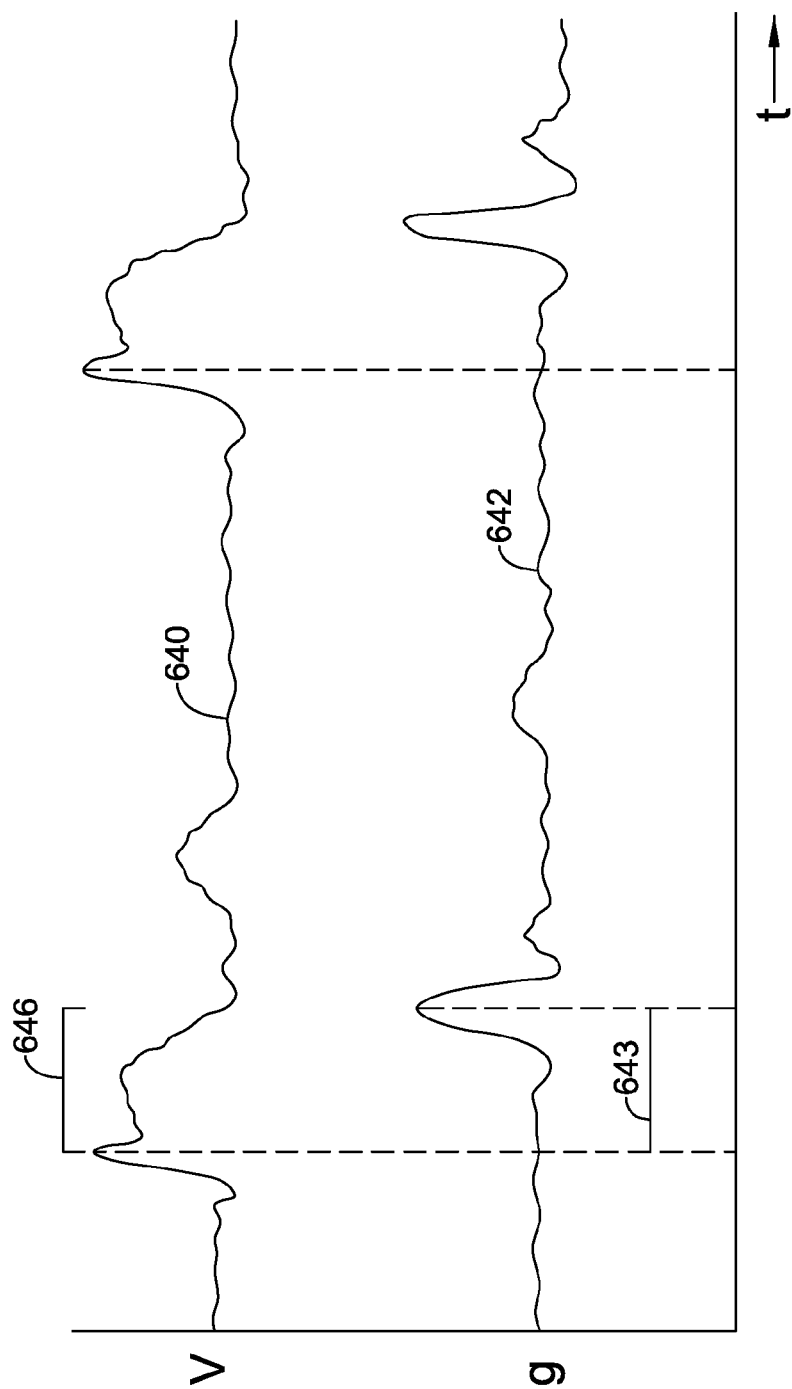
FIG. 10 depicts a graph including a cardiac electrical signal including elevated S-T segments and an accelerometer signal shown on the same time axis.

The delay parameter, represented by delay period 515 in FIG. 6, may represent the time delay between detection of a cardiac electrical event 511' (e.g. R-wave) and a peak of the accelerometer signal or where the accelerometer signal crosses an amplitude threshold. In some cases, an MI may cause the delay period 515 to lengthen for one or more of the sensed accelerometer signals 504'-510'. For instance, delay period 515 of FIG. 6 for signal 510' may be shorter than delay period 643 of FIG. 10 showing an example cardiac electrical signal and accelerometer signal after an MI has occurred.

The vector map may include a series of vectors determined based on the sensed accelerometer signals. For instance, where LCP 100 uses a three-axis accelerometer, LCP 100 may use accelerometer signals 504', 506', 508' and/or 510' sensed during sensing periods 512a'-512d' over time to determine a series of three-dimensional vectors forming a vector map.

In general, the baseline template may include any one of these determined baseline characteristics or any combination of these characteristics.

When developing the baseline template(s), it is contemplated that the accelerometer signals 504', 506', 508' and 510' may be repeatedly sensed over multiple heartbeats, and the resulting accelerometer signals 504', 506', 508' and 510' may be used to derive the baseline template(s). For example, the accelerometer signals 504', 506', 508' and 510' may be sensed over ten heartbeats, and then may be averaged, sometimes with a standard deviation or the like, when deriving the baseline template(s). This is just one example.

As described, LCP 100 may be the device that determines the baseline template. For instance, LCP 100 may determine one or more of the baseline characteristics based on the sensed accelerometer signals and/or the sensed cardiac electrical signal. However, in other embodiments, LCP 100 may communicate the sensed accelerometer signals and/or the sensed cardiac electrical signals to another device, such as pulse generator 406 and/or external support device 420. Pulse generator 406 and/or external support device 420, then, may determine the baseline template based on the received signals.

After the baseline template has been determined, the baseline template may be stored in a memory, as shown at 606. In some embodiments, LCP 100 may store the determined baseline template in its own memory. In alternative embodiments, LCP 100 may communicate the determined baseline template to another device, such as pulse generator 406 or external support device 420, and the receiving device may store the determined baseline template in its own memory.

Once the baseline template has been stored in a memory, LCP 100 may sense a signal generated by the accelerometer during a test period subsequent to the baseline period that reflects movement of the patient's heart during the test period, as shown at 607. For example, during a time period that occurs after the baseline time period, LCP 100 may sense the accelerometer signals and/or the cardiac electrical signal(s), which can be used to determine if the patient has suffered from an MI. During the test period, as during the baseline period, LCP 100 may be configured to sense the accelerometer signals and/or the cardiac electrical signal(s) during portions of the cardiac cycle corresponding to sensing periods 512a'-512d'.

In some cases, the method may include determining a test template based on one or more characteristics of the accelerometer signals during the test period, as at 610. LCP 100, pulse generator 406, and/or external support device 420 (or other devices that may be a part of system 400, such as implantable loop recorder) may determine the test template in a similar manner to how the baseline template is determined. In examples where the test template includes a delay parameter, the determining device may further utilize a cardiac electrical signal sensed during the test period. In some cases, the test template may simply be the sensed accelerometer signals themselves, and/or an average of the sensed accelerometer signals over a plurality of heartbeats.

A device may compare the baseline template with the test template and determine if an MI has occurred in the patient's heart based on the comparison, as shown at 612. In some instances, it may be LCP 100 doing the determining, pulse generator 406 doing the determining, or external support device 420 doing the determining. In some cases, the determining may be split among the various devices.

In some embodiments, the comparison may include performing one or more correlation analyses. For instance, where the baseline template and the test template include the accelerometer signals themselves, the comparison may include a cross-correlation analysis between the baseline accelerometer signal template or templates and the test accelerometer signal template or templates, resulting in a correlation parameter. Where the baseline template and the test template include one or more determined characteristics, the comparison may include a comparison of the differences between one or more of the determined characteristics of the baseline template and the test template.

As used herein, determining a difference between two values may include subtracting either value from the other. The process may further include determining an absolute value of the difference. Accordingly, comparison of determined differences to thresholds may correspond to comparing the absolute value of the determined difference to a threshold. In other embodiments, however, the determined difference may be directly compared to a threshold. In some of these embodiments, the threshold may have a negative value.

In embodiments where the comparison includes producing a correlation parameter, the comparing device may compare the correlation parameter to a threshold. If the correlation parameter is below the threshold, the device may determine that the patient has suffered from an MI. Where the comparison includes comparing a difference between the baseline template and the test template, e.g. comparing a difference between one or more of the determined characteristics of the baseline template and the test template, the difference may be compared to one or more thresholds. As one example, the comparing device may compare the difference between the baseline average amplitude of the accelerometer signal or signals and the test average amplitude of the accelerometer signal or signals to a threshold. If the difference is greater than the threshold, the device may determine that an MI has occurred.

In some embodiments, the comparing device may be able to distinguish between MIs that have occurred locally to LCP 100 within the heart or remote from LCP 100 within the heart. For instance, an MI that occurs locally to LCP 100 within the heart may cause the average amplitude of the accelerometer signal or signals to be relatively lower than the baseline average amplitude of the accelerometer signal or signals, as the infarcted tissue may contract to a lesser extent during contraction. However, an MI that occurs remote to LCP 100 within the heart may cause the average amplitude of the accelerometer signal or signals to be relatively higher than the baseline average amplitude of the accelerometer signal or signals, as the heart tissue locally to LCP 100 may contract to a greater extent to make up for the lower relative contraction of the infarcted tissue. Accordingly, in some embodiments, the comparing device may compare the difference between the baseline and the test average amplitude of the accelerometer signal or signals (e.g. the test average amplitude of the accelerometer signal or signals subtracted from the baseline average amplitude of the accelerometer signal or signals) to multiple thresholds, such as a high threshold and a low threshold. In these embodiments, the comparing device may determine that an MI has occurred if the difference is either above the high threshold or below the low threshold. In some additional embodiments, the comparing device may further determine that the MI occurred remotely to LCP 100 if the difference is below the low threshold and determine the MI occurred locally to LCP 100 if the difference is above the high threshold.

Figure 8:
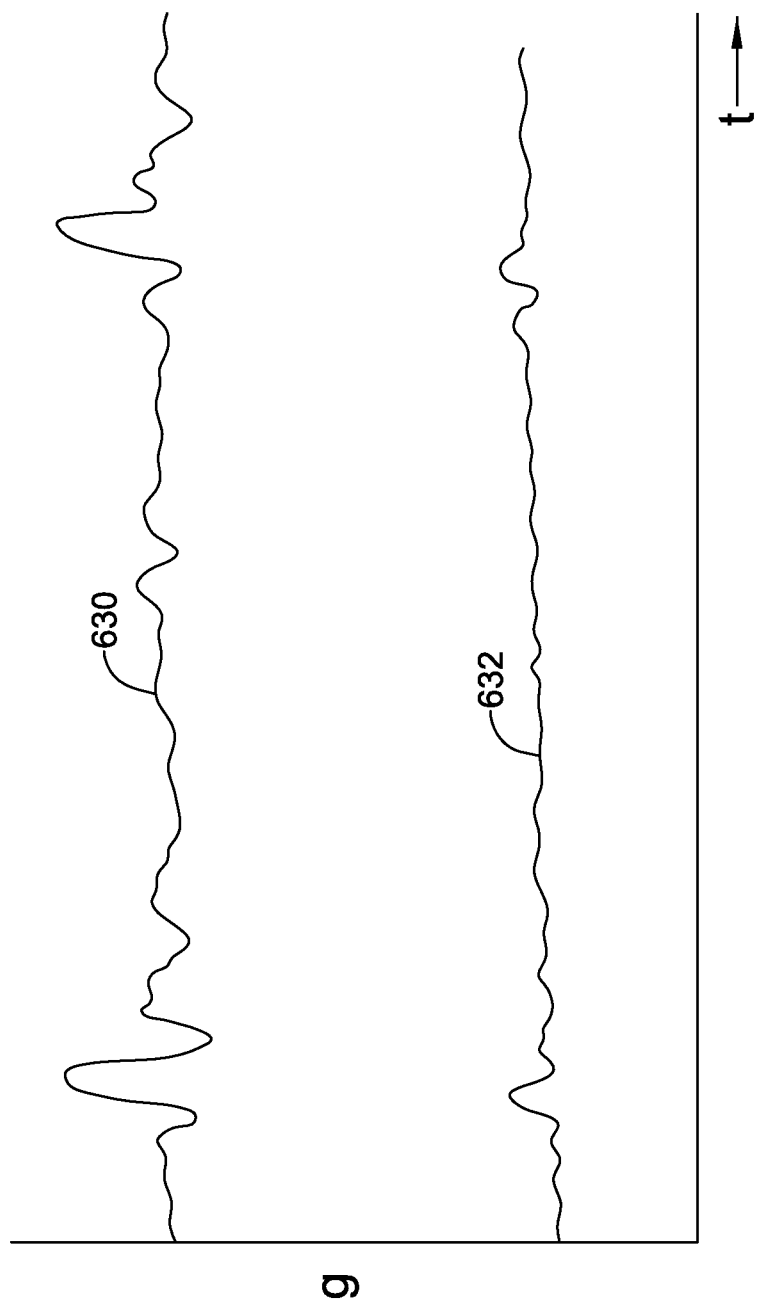
FIG. 8 depicts a graph including an accelerometer signal sensed during a baseline period and an accelerometer signal sensed during a test period after an occurrence of an MI locally to a device sensing the accelerometer signals.
Figure 9:
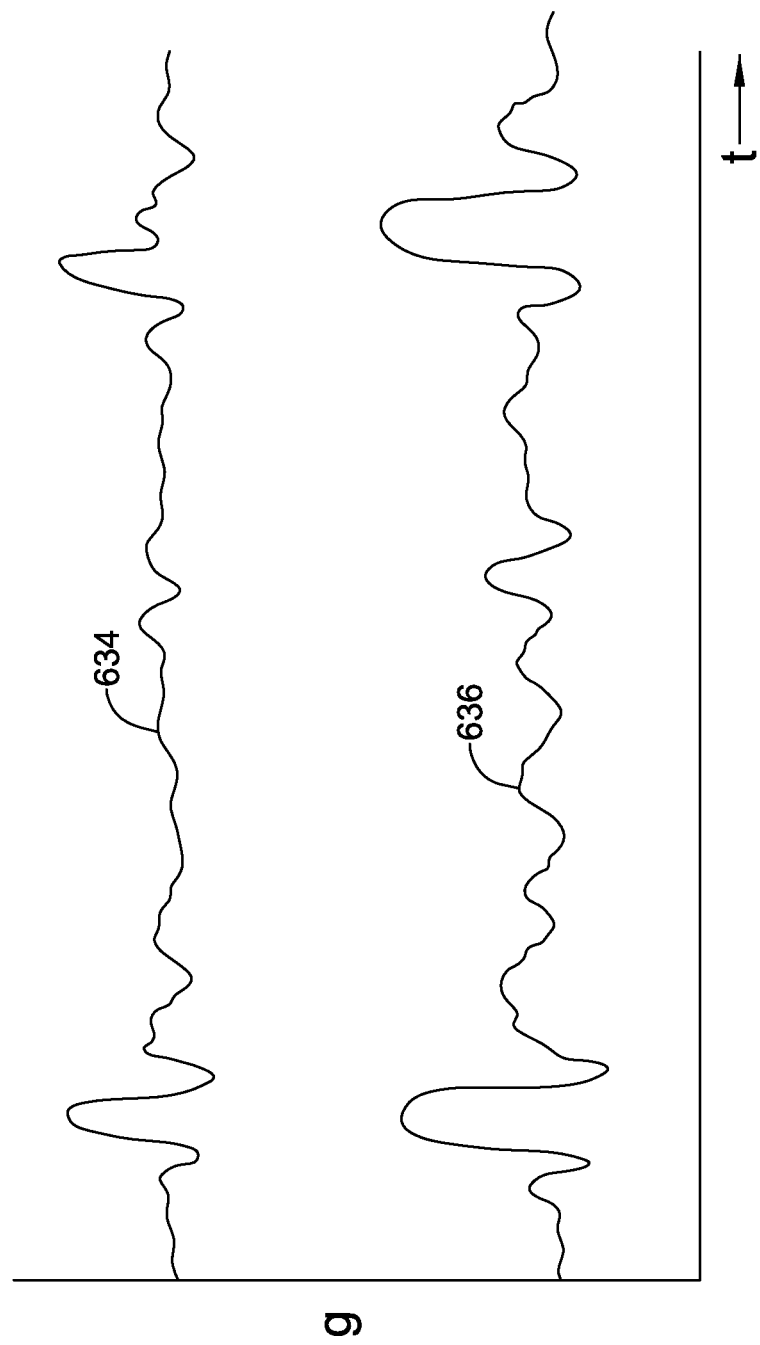
FIG. 9 depicts a graph including an accelerometer signal sensed during a baseline period and an accelerometer signal sensed during a test period after an occurrence of an MI remote to a device sensing the accelerometer signals.

FIG. 8 is a graph depicting an example accelerometer signal 630 sensed during the baseline period and an example accelerometer signal 632 sensed during a test period. Example accelerometer signal 632 represents an example accelerometer signal after the heart has experienced an MI locally to LCP 100. FIG. 9 is a graph depicting an example accelerometer signal 634 sensed during the baseline period and an example accelerometer signal 636 sensed during a test period. Example accelerometer signal 636 represents an example accelerometer signal after the heart has experienced an MI remote to LCP 100. As can be seen, accelerometer signal 632 has a relatively lower maximum amplitude and lower average amplitude than accelerometer signal 630. Additionally, accelerometer signal 636 has a relatively higher maximum amplitude and average amplitude than accelerometer signal 634.

In a similar manner, the comparing device may use the determined baseline maximum amplitude, integral, and/or phase compared to the test maximum amplitude, integral, and/or phase to determine whether an MI has occurred. For instance, the comparing device may compare differences between determined characteristics in the baseline template and determined characteristics in the test template to one or more thresholds to determine whether an MI has occurred.

Where the comparing device uses a vector map, the comparing device may compare differences in baseline vectors and test vectors that were determined at the same time within a sensing period. For instance, the comparing device may compare a baseline vector determined ten milliseconds into a sensing period with a test vector determined ten milliseconds into a sensing period. If the comparing device determines that the difference between the two vectors exceeds a threshold difference, the device may determine that an MI has occurred. In additional embodiments, the device may compare baseline and test vectors determined at multiple locations within a sensing period. For instance, the comparing device may compare five, eight, ten, fifteen, twenty, or any other suitable number of determined baseline and test vectors across the sensing period. In some of these embodiments, the comparing device may determine that an MI has occurred if any of the comparisons between the baseline and test vectors exceeds a threshold difference. In other embodiments, the comparing device may determine that an MI has occurred if a threshold number of the comparisons between baseline and test vectors exceed the threshold difference. In additional or alternative embodiments, the comparing device may track a total difference parameter that sums the differences between the baseline and test vectors. The comparing device may compare the total difference parameter to a threshold value and determine that an MI occurred if the total difference parameter exceeds the threshold value. These are just some examples.

In any of these manners, the comparing device may determine that an MI has occurred. Once the device has determined that an MI has occurred, the comparing device may cause an indication to be displayed on a display indicating that an MI has occurred in the patient's heart, as shown at 614. For instance, where the comparing device is LCP 100 or pulse generator 420, the device may generate an alarm signal and communicate the alarm signal to a device that is external to the patient and includes a display for viewing by a user, such as external support device 420 as one example. Upon receipt of the alarm signal, the external device may cause an indication to be displayed on the display alerting a user that an MI has occurred. Where the comparing device is the external device, the external device may simply cause an indication to be displayed on its own display alerting a user that an MI has occurred. In at least some embodiments, the external device may be a cellular telephone.

Other contemplated embodiments include variations on the above described method for determining whether an MI has occurred. For instance, in some embodiments, the baseline template and the test template may include multiple determined characteristics, and the comparing device may compare multiple of the determined characteristics to determine whether an MI has occurred. In some of these embodiments, the comparing device may not determine that an MI has occurred unless multiple of the determined characteristics indicate that an MI has occurred. As one example, the comparing device may only determine that an MI has occurred after determining that differences between two determined characteristics of the baseline and test templates fall above or below respective threshold values. For instance, the correlation parameter and the difference between average amplitudes of the baseline and test templates may need to fall above or below respective threshold values. However, more generally, the comparing device may use any two of the disclosed determined characteristics and the correlation parameter to make the determination about whether an MI has occurred. In other embodiments, the determining device may use three, four, or five of the determined characteristics and/or the correlation parameter, or all of the determined characteristics and/or the correlation parameter in determining that an MI has occurred.

In some instances, the method used to determine whether an MI has occurred may include creating separate baseline and test templates based on intrinsic cardiac electrical events and paced cardiac electric events. For instance, the response of the heart, and hence the accelerometer signal or signals and/or the cardiac electrical signal sensed by LCP 100, may be different depending on whether a cardiac electrical event is an intrinsic cardiac electrical event or is in response to delivered pacing pulse. In these embodiments, the device that determines the baseline templates and the test templates may determine a baseline template and a test template using signals sensed after an intrinsic cardiac electrical event and a baseline template and a test template using signals sensed after a paced cardiac electrical event. In some cases, the device that determines whether an MI has occurred may determine that an MI has occurred based on comparisons between either of the determined baseline and test templates. In some cases, the comparing device may only determine that an MI has occurred after comparisons between baseline and test templates determined using signals sensed after an intrinsic cardiac electrical event and comparisons between baseline and test templates determined using signals sensed after a paced cardiac electrical event indicate that an MI has occurred.

In some cases, determining that a difference between a baseline template and a test template falls above or below a threshold may only be one step in the process to determine whether an MI has occurred. For instance, a method may further include analysis of one or more other sensed signals, as signals other than the sensed accelerometer signals may change after an MI has occurred. FIG. 10 depicts an example graph including cardiac electrical signal 640 and accelerometer signal 642, both sensed after an MI has occurred. The device that determines whether an MI has occurred may use cardiac electrical signal 640 itself to determine whether an MI has occurred. For instance, the specific morphology of a sensed cardiac electrical signal may differ before and after an MI. One difference that commonly occurs is an elongated and/or elevated S-T segment, as depicted in region 646 of cardiac electrical signal 640. In some embodiments, the determining device may compare a baseline cardiac electrical signal template with a test cardiac electrical signal or signal template, for instance using one or more correlation analyses, and determine one or more correlation parameters. The determining device may then compare the one or more determined correlation parameters to a threshold and, based on this comparison, determine whether an MI has occurred. In some instances, the template and the test signal may only include a portion of the sensed cardiac electrical signal, such as the portion encompassing the S-T segment of the cardiac electrical signal within region 646. However, it should be understood that this is only one example in which the comparing device may determine an occurrence of an elevated S-T segment.

Figure 11:
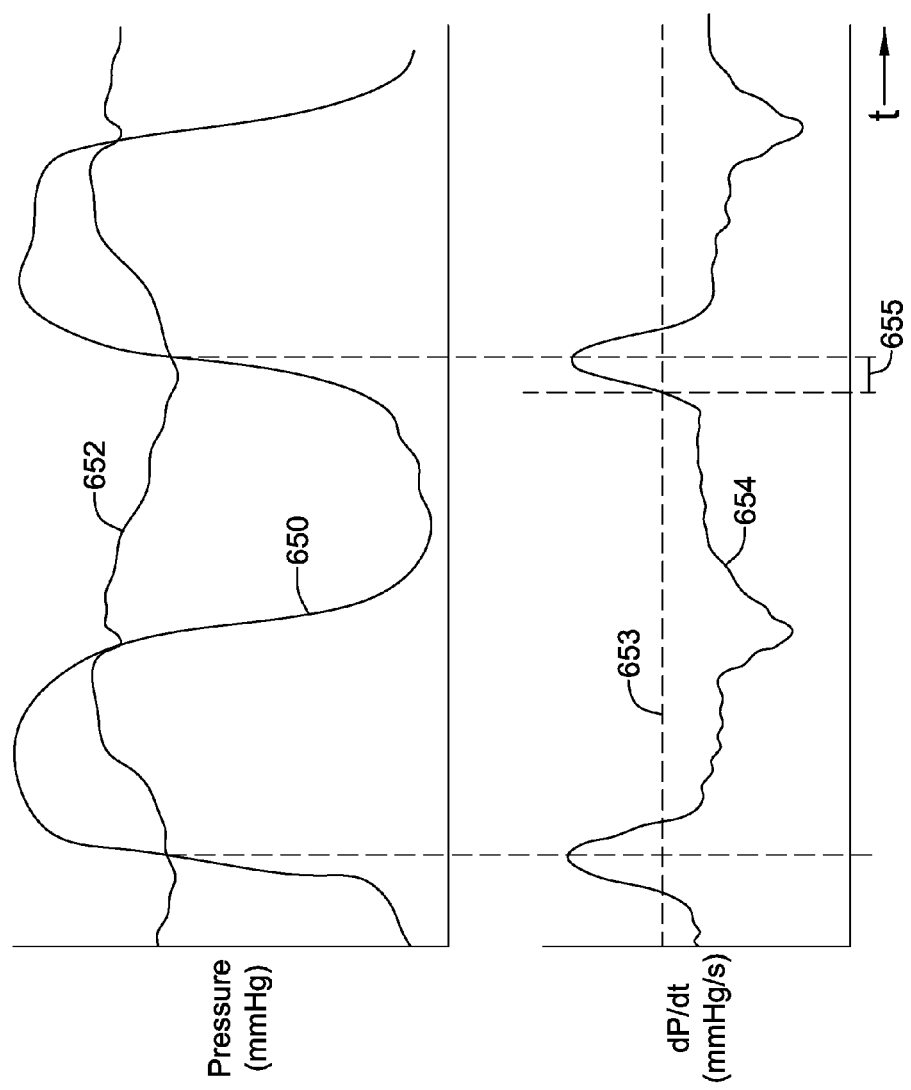
FIG. 11 depicts a graph of left ventricular pressure, aortic pressure, and a derivative of left ventricular pressure on the same time axis.

In some additional or alternative embodiments, the determining device may further use a determined isovolumic contraction period to determine whether an MI has occurred. For instance, LCP 100 may include a pressure sensor and may sense intra-ventricular pressure. FIG. 11 depicts intra-ventricular pressure signal 650 along with intra-aorta pressure 652. FIG. 11 further depicts dp/dt signal 654 representing a derivative of the intra-ventricular pressure signal, which may be determined by LCP 100 or another device based on receipt of intra-ventricular pressure signal 650 transmitted by LCP 100. Based on sensed intra-ventricular pressure signal 650, a device may determine an isovolumic contraction period during the baseline time period and a test time period. In the example of FIG. 11, period 655 may represent the isovolumic contraction period. Illustrative period 655 is the period of time after dp/dt signal 654 rises above threshold 653 until dp/dt signal 654 reaches a peak. After an MI, the length of the isovolumic contraction period, e.g. period 655, may lengthen. Accordingly, the determining device may compare the isovolumic contraction period determined during the baseline time period along with an isovolumic contraction period determined during a test period. If the difference between these two parameters is greater than a threshold amount, the device may determine that an MI has occurred.

In some cases, the determining device may use the comparison between the isovolumic contraction period determined during the baseline time period and the isovolumic contraction period determined during a test period as a basis for determining that the heart is experiencing ischemic conditions. For instance, lengthening of the isovolumic contraction period may indicate ischemia as opposed to an occurrence of an MI. Accordingly, a device may determine that the heart is experiencing ischemic conditions if the difference between the isovolumic contraction period determined during the baseline time period and the isovolumic contraction period determined during a test period is greater than a threshold amount. In some embodiments, the threshold amount for determining that the heart is experiencing ischemic conditions may be less than the threshold amount for determining whether there has been an occurrence of an MI. In other embodiments, however, the thresholds may be the same. In some embodiments where the thresholds are the same, the device may determine that the heart is experiencing ischemic conditions rather than determining an occurrence of an MI when no other signals (e.g. cardiac and/or accelerometer signals) or signal characteristics indicate that an MI has occurred. Where the device determines that the heart is experiencing ischemic conditions, the device may output an alarm signal indicating that the heart is experiencing ischemic conditions.

Figure 12:
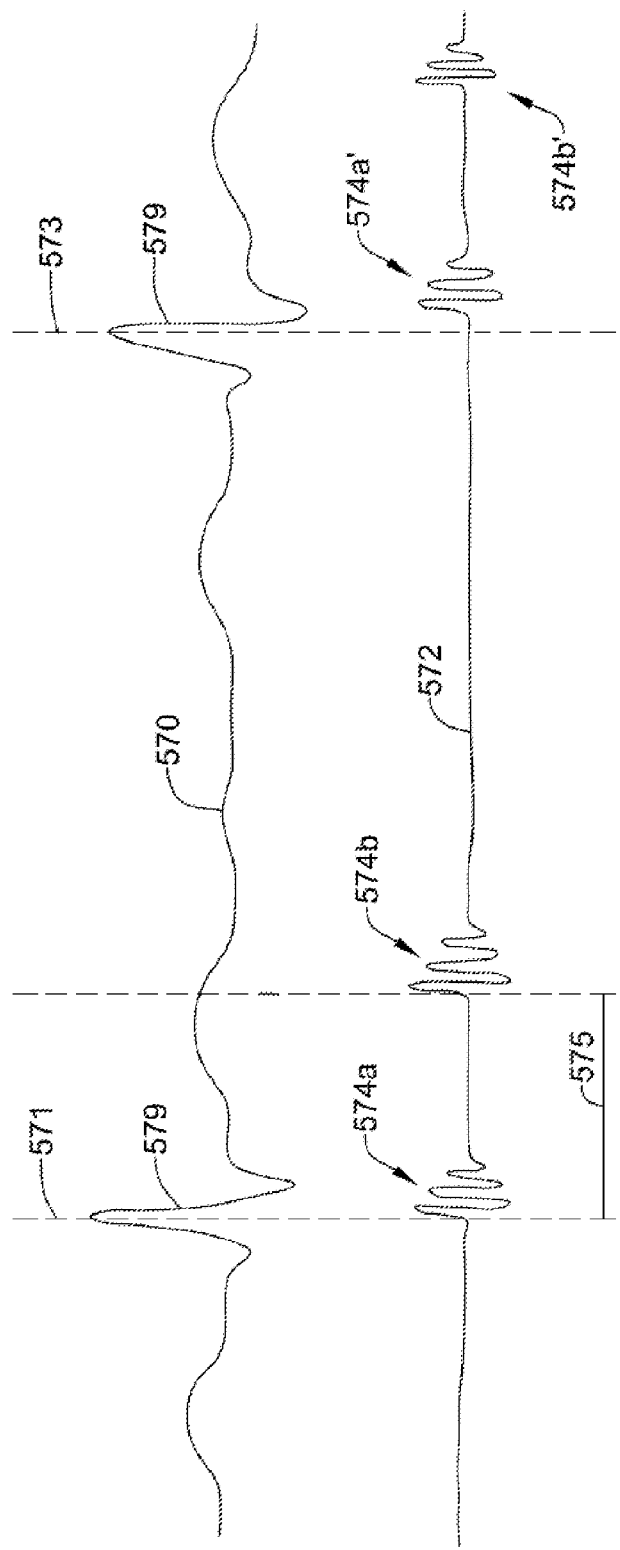
FIG. 12 depicts a graph including a cardiac electrical signal and a heart sounds signal on the same time axis illustrating the timing of features between the two signals.

In some cases, the determining device may use heart sounds to help determine whether an MI has occurred. For instance, a device, using the accelerometer signal or signals sensed by LCP 100, may be able to determine a heart sounds signal (e.g. first heart sound, second heart sound). FIG. 12 depicts sensed cardiac electrical signal 570 along with heart sounds signal 572. Similar to the accelerometer signal or signals and the cardiac electrical signal, heart sounds signal 572 may differ before and after an MI. For instance, heart sounds signal 572 may have a different morphology before and after an MI. Additionally, or alternatively, one or more features of heart sounds signal 572 may occur at different times in relation to each other, or in relation to one or more features of cardiac electrical signal 570. As one example, in a healthy heart, heart sound features 574a and 574a' may begin in close relation to peaks of cardiac electrical events 579, represented by lines 571 and 573. However, after an MI, there may be a delay between a peak of a cardiac electrical event and the beginning of a heart sound feature, such as features 574a or 574a'. Another indication may be the time between heart sound features 574a and 574b or 574a' and 574b', represented by time period 575. For instance, after an MI, time period 575 may become shorter or longer.

Accordingly, the device that determines whether an MI has occurred may alternatively or additionally use differences in a heart sounds signal template determined during the baseline period, e.g. a baseline heart sounds signal template, and a heart sounds signal template determined during a test period, e.g. a test heart sounds signal template, to determine whether an MI has occurred. For instance, the determining device may compare the heart sounds signal templates using a correlation analysis to produce a correlation parameter. The device may compare the correlation parameter to a threshold, and determine that an MI has occurred if the parameter is lower than the threshold. Additionally, or alternatively, the determining device may determine one or more characteristics or timings of the heart sounds signal templates, such as a timing between a peak of a cardiac electrical event and a beginning of a heart sounds feature or the timing between two heart sounds features. The determining device may then compare the one or more determined timings to one or more thresholds to determine whether an MI has occurred. For instance, the device may determine an MI has occurred if the difference between the timing of the peak of a cardiac electrical event and a beginning of a heart sounds feature or the timing between two heart sounds features is greater than a threshold.

In some embodiments, the device that determines whether an MI has occurred may determine that an MI has occurred after any of the accelerometer signals, the cardiac electrical signals, the heart sounds signals, and/or the isovolumic contraction period indicate that an MI has occurred. However, in other embodiments, the determining device may only determine that an MI has occurred if multiple of the accelerometer signals, the cardiac electrical signals, the heart sounds signals, and the isovolumic contraction period indicate that an MI has occurred. For instance, the determining device may determine that an MI has occurred after determinations made based on the accelerometer signals and the cardiac electrical signals indicate that an MI has occurred. However, this is just one example. In other embodiments, the determining device may only determine that an MI has occurred after any two of the accelerometer signals, the cardiac electrical signals, the heart sounds signals, and the isovolumic contraction period indicate that an MI has occurred. In still other embodiments, the determining device may only determine that an MI has occurred after any three of the accelerometer signals, the cardiac electrical signals, the heart sounds signals, and the isovolumic contraction period, or all of the accelerometer signals, the cardiac electrical signals, the heart sounds signals, and the isovolumic contraction period, indicate that an MI has occurred.

In some cases, the determining device may employ a cascading scheme for determining whether an MI has occurred. For example, the determining device may initially monitor only one (or a few) of the accelerometer signals, the cardiac electrical signals, the heart sounds signals, and/or the isovolumic contraction period to determine whether an MI has occurred. After the determining device has determined that the initially monitored signal(s) or period indicate that an MI has occurred, the determining device may use a second one of the accelerometer signals, the cardiac electrical signals, the heart sounds signals, and/or the isovolumic contraction period to determine whether an MI has occurred. If the second one of the accelerometer signals, the cardiac electrical signals, the heart sounds signals, and/or the isovolumic contraction period also indicates that an MI has occurred, the determining device may ultimately determine that an MI has occurred and generate an alarm signal. In some cases, the determining device may switch to using a third one of accelerometer signals, the cardiac electrical signals, the heart sounds signals, and/or the isovolumic contraction period to determine whether an MI has occurred before generating an alarm signal. In some cases, the determining device may also use the fourth of the accelerometer signals, the cardiac electrical signals, the heart sounds signals, and/or the isovolumic contraction period to determine whether an MI has occurred before generating an alarm signal. In general, the determining device may use the accelerometer signals, the cardiac electrical signals, the heart sounds signals, and/or the isovolumic contraction period in any order or combination to determine whether an MI has occurred and to generate an alarm signal.

In another example, the determining device may initially monitor a cardiac electrical signal and look for an elongated and/or elevated ST segment of the cardiac electrical signal. For instance, the determining device may compare a portion of the cardiac electrical signal containing the ST segment to one or more templates of an elongated and/or elevated ST segment and determine that the portion of the cardiac electrical signal contains an elongated and/or elevated ST segment based on a threshold fit to the one or more templates. Once an elongated and/or elevated ST segment is detected, the determining device may turn on the accelerometer of the LCP to monitor the accelerometer signals to confirm whether or not an MI has occurred. In any event, it is contemplated that the determining device may save some energy by only monitoring or using a single or small number of signals to initially detect if an MI occurred, and then monitor other signals to confirm whether an MI occurred.

Another variation to the disclosed methods may include, before determining whether an MI has occurred, determining an activity level, heart rate, and/or posture of the patient.

For instance, during the baseline period, LCP 100 may be configured to determine and store a baseline activity level, a baseline heart rate, and a baseline posture. In these examples, before switching into an MI mode, LCP 100 may determine a test activity level, a test heart rate, and a test posture. If any one of these test parameters differs from their corresponding baseline parameter by more than a threshold amount, LCP 100 may skip entering the MI mode. For instance, as described, LCP 100 may be configured to enter an MI mode based periodically, intermittently or based on a trigger. Once the period expires or LCP 100 receives a trigger, LCP 100 may determine one or more of the test activity level, a test heart rate, and a test posture.

LCP 100 may skip entering the MI mode and wait for another trigger or a next scheduled time period if LCP 100 determines that one of activity level, heart rate, or posture test parameters differ from their corresponding baseline parameter by more than a threshold amount. In some cases, it may be desirable to operate in this manner because the signals used to determine whether an MI has occurred may differ based on the activity level of the patient, the heart rate of the patient, and/or the posture of the patient. Accordingly, where any of these parameters differ by greater than a threshold amount from their corresponding baseline parameter, the signals sensed during the test period may differ due to the differences in activity level, the heart rate, and/or the posture rather than because of an occurrence of an MI. LCP 100 may then reduce or eliminate false positive determinations of occurrences of MI by only entering MI mode when a detected activity level, heart rate, and/or posture are similar to the activity level, heart rate, and/or posture during the baseline period. Rather than operating in this manner, the LCP 100 may be configured to compensate for the different activity level, heart rate, or posture test parameters when determining whether an MI occurred.

Those skilled in the art will recognize that the present disclosure may be manifested in a variety of forms other than the specific embodiments described and contemplated herein. For instance, as described herein, various embodiments include one or more modules described as performing various functions. However, other embodiments may include additional modules that split the described functions up over more modules than that described herein. Additionally, other embodiments may consolidate the described functions into fewer modules.

Although various features may have been described with respect to less than all embodiments, this disclosure contemplates that those features may be included on any embodiment. Further, although the embodiments described herein may have omitted some combinations of the various described features, this disclosure contemplates embodiments that include any combination of each described feature. Accordingly, departure in form and detail may be made without departing from the scope and spirit of the present disclosure as described in the appended claims.

What is claimed is:

1. A method of sensing for an occurrence of a myocardial infarction in a patient's heart using a leadless cardiac pacemaker that is affixed to the patient's heart, the method comprising:

sensing, by the leadless cardiac pacemaker, a baseline first sensor signal generated via a first sensor of the leadless cardiac pacemaker during a baseline period, the first sensor comprising one or more of a cardiac electrical signal sensor, a heart sound sensor, and an isovolumic contraction period sensor;

sensing, by the leadless cardiac pacemaker, a baseline accelerometer signal generated via an accelerometer of the leadless cardiac pacemaker during the baseline period that reflects movement of the patient's heart during the baseline period;

determining a baseline template based on one or more characteristics of the baseline first sensor signal and the baseline accelerometer signal;

storing the baseline template in a memory;

sensing, by the leadless cardiac pacemaker, the baseline first sensor signal generated via the first sensor during a first test period subsequent to the baseline period;

determining a first test template based on one or more characteristics of the first sensor signal during the test period;

comparing the first test template with the baseline template, and based on the comparison, determining if a myocardial infarction may have occurred in the patient's heart;

when it is determined that a myocardial infarction may have occurred in the patient's heart, then:

sensing, by the leadless cardiac pacemaker, the accelerometer signal generated via the accelerometer during a second test period subsequent to the first test period that reflects movement of the patient's heart during the second test period;

determining a second test template based on one or more characteristics of the accelerometer signal during the second test period;

comparing the second test template with the baseline template, and based on the comparison, determining if a myocardial infarction occurred in the patient's heart;

communicating information from the leadless cardiac pacemaker to an external device; and when it is determined that a myocardial infarction occurred in the patient's heart based on the comparison of the second test template with the baseline template, displaying an indication on a display of the external device that a myocardial infarction occurred in the patient's heart.

2. The method of claim 1, further comprising:

transmitting an output signal for reception by the external device that is located external to the patient indicating that a myocardial infarction occurred in the patient's heart.

3. The method of claim 2, wherein the external device is a device programmer.

4. The method of claim 2, wherein the external device is a cellular telephone.

5. The method of claim 1, wherein the memory is part of the leadless cardiac pacemaker.

6. The method of claim 1, wherein the baseline template and the first test template are compared by the leadless cardiac pacemaker.

7. The method of claim 1, wherein the leadless cardiac pacemaker determines if a myocardial infarction occurred in the patient's heart.

8. The method of claim 1, wherein the memory is part of the external device that is located external to the patient.

9. The method of claim 1, wherein the baseline template and the first test template are compared by the external device that is located external to the patient.

10. The method of claim 1, wherein the external device is located external to the patient and determines if a myocardial infarction occurred in the patient's heart.

11. A method of sensing for an occurrence of a myocardial infarction in a patient's heart using a leadless cardiac pacemaker that is affixed to the patient's heart, the method comprising:

determining when one or more baseline conditions exist;

when the one or more baseline conditions exist, then:

sampling, by the leadless cardiac pacemaker, a baseline accelerometer signal generated via an accelerometer of the leadless cardiac pacemaker during a baseline period that reflects movement of the patient's heart during the baseline period;

storing in a memory one or more characteristics of the baseline accelerometer signal sensed during the baseline period;

after storing in the memory the one or more characteristics of the baseline accelerometer signal sensed during the baseline period, determining when the one or more baseline conditions again exist;

when the one or more baseline conditions again exist:

sampling, by the leadless cardiac pacemaker, an accelerometer signal generated via the accelerometer that reflects movement of the patients' heart during a test period;

comparing one or more characteristics of the accelerometer signal sampled during the test period with the one or more characteristics of the baseline accelerometer signal sampled during the baseline period, and based on the comparison, determining if a myocardial infarction occurred in the patients' heart;

communicating information from the leadless cardiac pacemaker to an external device; and when it is determined that a myocardial infarction occurred in the patient's heart, displaying an indication on a display of the external device that a myocardial infarction occurred in the patient's heart.

12. The method of claim 11, wherein the memory is part of the leadless cardiac pacemaker.

13. The method of claim 11, wherein the one or more characteristics of the accelerometer signal sampled during the test period and the one or more characteristics of the baseline accelerometer signal sampled during the baseline period are compared by the leadless cardiac pacemaker.

14. The method of claim 11, wherein the leadless cardiac pacemaker determines if a myocardial infarction occurred in the patient's heart.

15. The method of claim 11, wherein the external device is located external to the patient and determines if a myocardial infarction occurred in the patient's heart.

16. The method of claim 11, wherein the one or more baseline conditions comprises one or more of a baseline activity level condition, a baseline heart rate condition, and a baseline posture condition.

* * * * *